(12) United States Patent
Ralph et al.

(10) Patent No.: US 8,080,042 B2
(45) Date of Patent: Dec. 20, 2011

(54) CRANIOTOMY CLOSURES AND PLUGS

(75) Inventors: James D. Ralph, Bethlehem, PA (US); Thomas N. Troxell, Pottstown, PA (US)

(73) Assignee: Biodynamics, LLC, Englewood, NJ (US)

( * ) Notice: Subject to any disclaimer, the term of this patent is extended or adjusted under 35 U.S.C. 154(b) by 0 days.

(21) Appl. No.: 12/710,541

(22) Filed: Feb. 23, 2010

(65) Prior Publication Data

US 2010/0179553 A1     Jul. 15, 2010

Related U.S. Application Data

(63) Continuation of application No. 11/333,102, filed on Jan. 17, 2006, now Pat. No. 7,833,253.

(51) Int. Cl.
*A61B 17/80*     (2006.01)
*A61F 2/02*     (2006.01)

(52) U.S. Cl. ........ 606/283; 606/284; 606/285; 606/286; 623/17.19

(58) Field of Classification Search ............ 606/60, 606/70, 71, 283–286; 403/397; 277/637, 277/640, 647, 598; 600/206–208; 623/17.17–19.19, 623/16.11, 23.63; 248/230.8, 230.9; 433/172, 433/173, 193; 132/53, 54
See application file for complete search history.

(56) References Cited

U.S. PATENT DOCUMENTS

| | | | |
|---|---|---|---|
| 986,543 A | 3/1911 | Burroughes |
| 1,105,105 A | 7/1914 | Sherman |
| 1,278,133 A | 9/1918 | Gammeter |
| 2,543,963 A | 3/1951 | Gaffin |
| 2,626,164 A | 1/1953 | West |
| 2,706,023 A | 4/1955 | Merritt |
| 2,795,387 A | 6/1957 | McNeely |
| 4,309,120 A | 1/1982 | Werthmann |
| 4,323,217 A | 4/1982 | Dochterman |
| 4,683,878 A | 8/1987 | Carter |
| 4,726,808 A | 2/1988 | Collins |
| 4,746,129 A | 5/1988 | Puccio |
| 4,966,599 A | 10/1990 | Pollock |
| 5,047,047 A | 9/1991 | Yoon |
| 5,413,577 A | 5/1995 | Pollock |
| 5,503,164 A | 4/1996 | Friedman |

(Continued)

FOREIGN PATENT DOCUMENTS

EP     1437098 A1     7/2004

(Continued)

OTHER PUBLICATIONS

Steller Technical Products, Lead-Free CAme, 2004, http://www.stellartechnical.com/csg3.html.

(Continued)

*Primary Examiner* — Eduardo C Robert
*Assistant Examiner* — Ellen C Hammond
(74) *Attorney, Agent, or Firm* — Lowenstein Sandler P.C.

(57) ABSTRACT

Strip fasteners and cranial plugs for use in reattaching a skull flap removed during brain surgery and methods of using the same. The strip fasteners are flexible and can be shaped to follow the perimeter contour of the skull flap. The cranial plugs can be used to reattach the skull flap or they can be installed after the skull flap is reattached using the strip fasteners. In some embodiments, the cranial plug(s) and strip fasteners can be installed at the same time. The strip fasteners and cranial plugs are designed to encourage bone growth and healing of the skull flap and they can be used to deliver medication and bone growth enhancement compositions to the surgical site.

4 Claims, 41 Drawing Sheets

U.S. PATENT DOCUMENTS

| | | | |
|---|---|---|---|
| 5,649,927 A | 7/1997 | Kipela et al. | |
| 5,669,912 A | 9/1997 | Spetzler | |
| 5,707,373 A | 1/1998 | Sevrain et al. | |
| 5,730,743 A | 3/1998 | Kirsch et al. | |
| 5,752,958 A | 5/1998 | Wellisz | |
| 5,797,915 A | 8/1998 | Pierson et al. | |
| 5,814,048 A | 9/1998 | Morgan | |
| 6,022,351 A | 2/2000 | Bremer et al. | |
| 6,068,631 A | 5/2000 | Lerch | |
| 6,102,347 A | 8/2000 | Benoit | |
| 6,190,389 B1 * | 2/2001 | Wellisz et al. | 606/86 B |
| 6,197,037 B1 * | 3/2001 | Hair | 606/151 |
| 6,258,091 B1 | 7/2001 | Sevrain et al. | |
| 6,325,803 B1 | 12/2001 | Schumacher et al. | |
| 6,328,743 B2 | 12/2001 | Lerch | |
| 6,350,284 B1 | 2/2002 | Tormala et al. | |
| 6,355,044 B1 | 3/2002 | Hair | |
| 6,364,881 B1 | 4/2002 | Apgar et al. | |
| 6,511,482 B1 | 1/2003 | Wellisz et al. | |
| 6,554,835 B1 | 4/2003 | Lee | |
| 6,582,435 B2 | 6/2003 | Wellisz et al. | |
| 6,589,244 B1 | 7/2003 | Sevrain et al. | |
| 6,641,588 B2 | 11/2003 | Citron et al. | |
| 6,652,531 B2 | 11/2003 | Wellisz et al. | |
| 6,682,533 B1 | 1/2004 | Dinsdale et al. | |
| 6,692,498 B1 | 2/2004 | Niiranen et al. | |
| 6,776,800 B2 * | 8/2004 | Boyer et al. | 623/23.63 |
| 6,821,279 B2 | 11/2004 | Di Emidio | |
| 6,855,169 B2 | 2/2005 | Boyer et al. | |
| 6,921,401 B2 | 7/2005 | Lerch et al. | |
| 7,090,459 B2 | 8/2006 | Bhate et al. | |
| 7,168,569 B2 | 1/2007 | Peresan | |
| 7,182,785 B2 | 2/2007 | Elsalanty et al. | |
| 2002/0040242 A1 | 4/2002 | Picha et al. | |
| 2002/0062127 A1 | 5/2002 | Schumacher et al. | |
| 2002/0120338 A1 | 8/2002 | Boyer, II et al. | |
| 2003/0100901 A1 | 5/2003 | Wellisz et al. | |
| 2003/0229349 A1 | 12/2003 | Wellisz et al. | |
| 2004/0034375 A1 | 2/2004 | Ruiz et al. | |
| 2004/0138591 A1 | 7/2004 | Iseki et al. | |
| 2004/0210224 A1 | 10/2004 | Ahmad et al. | |
| 2005/0033425 A1 | 2/2005 | Schwab | |
| 2005/0090831 A1 | 4/2005 | Ahmad et al. | |
| 2005/0240189 A1 | 10/2005 | Rosseau et al. | |
| 2006/0229610 A1 | 10/2006 | Piehl | |
| 2006/0285918 A1 | 12/2006 | Legat et al. | |
| 2008/0071323 A1 | 3/2008 | Lowry et al. | |
| 2008/0077133 A1 | 3/2008 | Schulze | |
| 2009/0076617 A1 | 3/2009 | Ralph et al. | |
| 2010/0179554 A1 | 7/2010 | Ralph et al. | |
| 2011/0054540 A1 | 3/2011 | Ralph et al. | |

FOREIGN PATENT DOCUMENTS

| | | |
|---|---|---|
| EP | 1437098 | 8/2006 |
| WO | WO 90/07304 | 7/1990 |
| WO | WO 9007304 | 7/1990 |

OTHER PUBLICATIONS

U.S. Appl. No. 12/710,614(US 2010-0179554) OA dated Apr. 6, 2011.

U.S. Appl. No. 12/710,614(US 2010-0179554) Response dated Jul. 6, 2011.

U.S. Appl. No. 12/249,005 (US 2009-0076617) OA dated Apr. 6, 2011.

U.S. Appl. No. 12/249,005 (US 2009-0076617) Response dated Jul. 6, 2011.

U.S. Appl. No. 12/942,444 (US 2011-0054540) OA dated May 13, 2011.

* cited by examiner

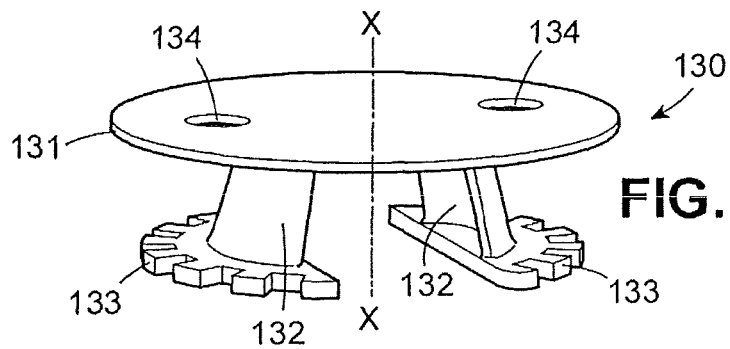
FIG. 13
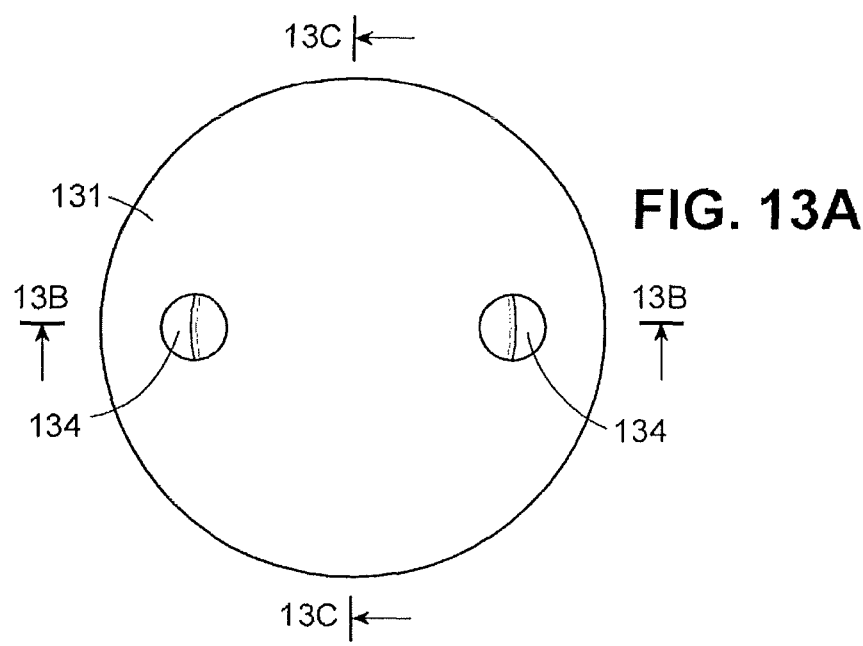
FIG. 13A
FIG. 13B
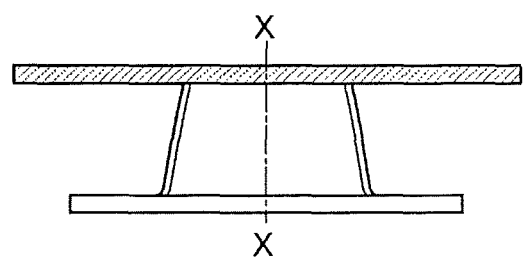
FIG. 13C

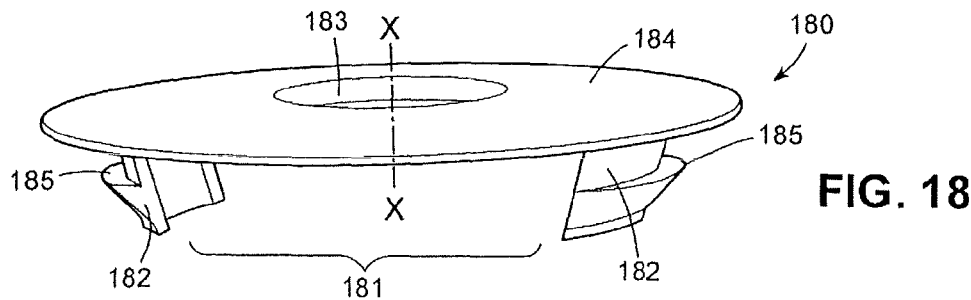
FIG. 18
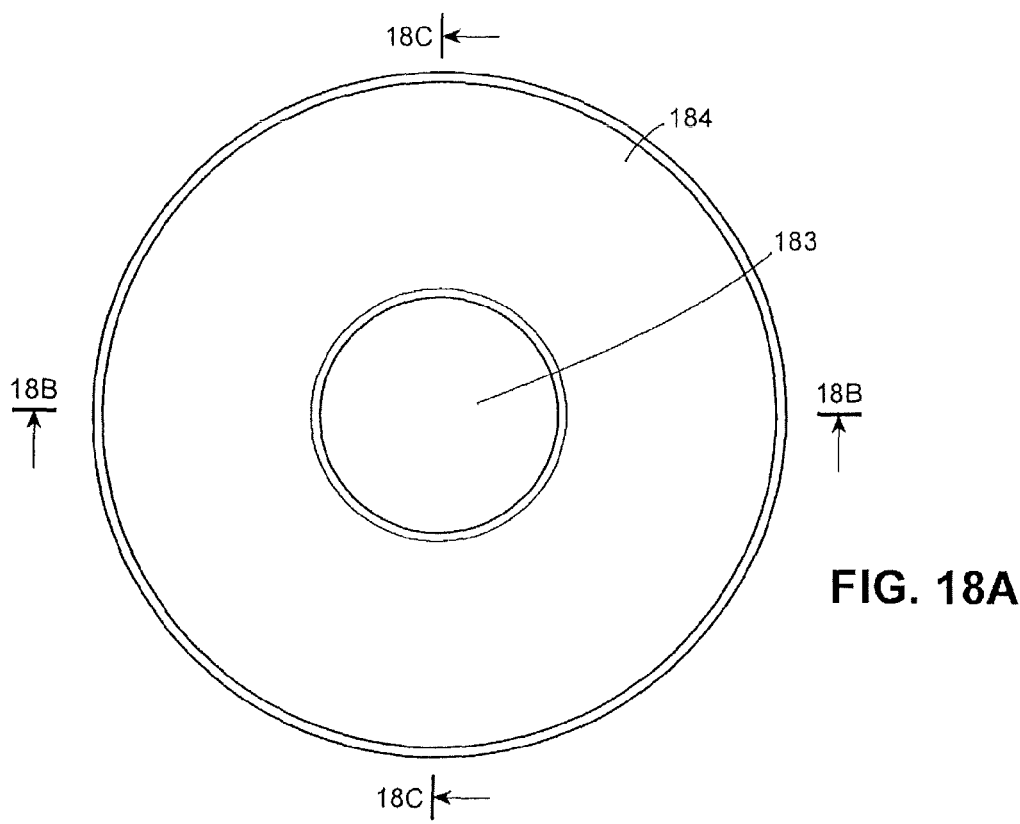
FIG. 18A
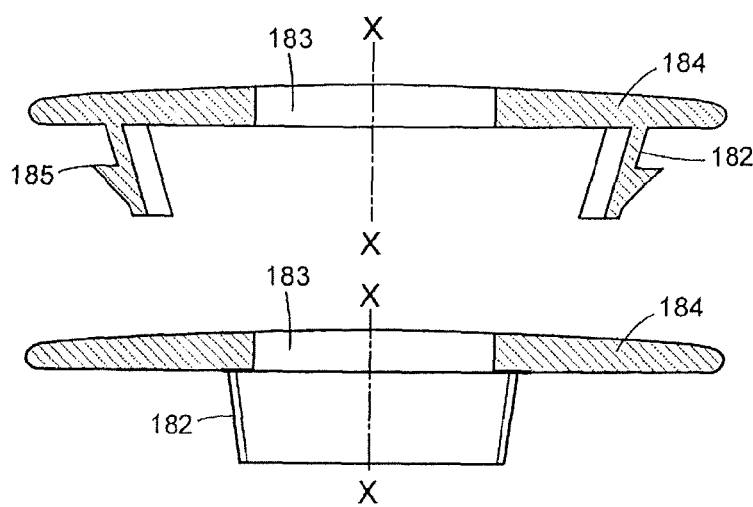
FIG. 18B
FIG. 18C

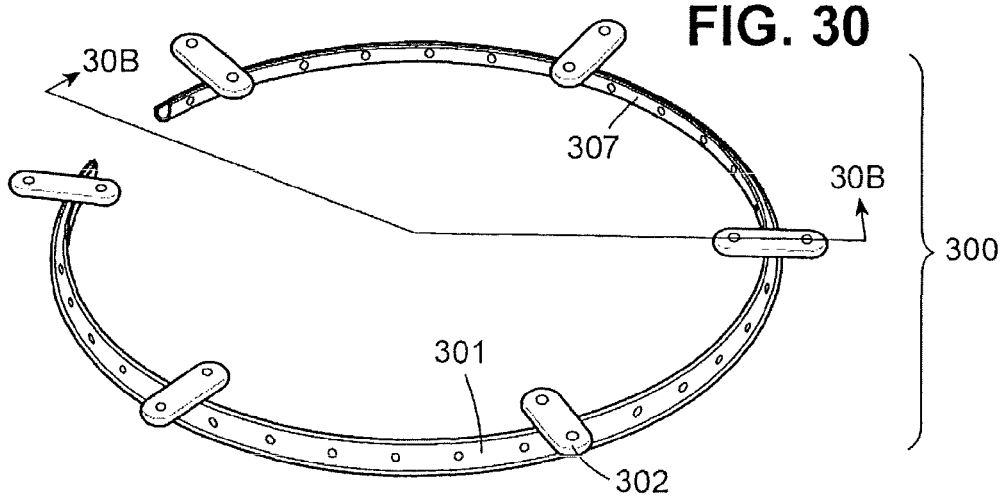
FIG. 30
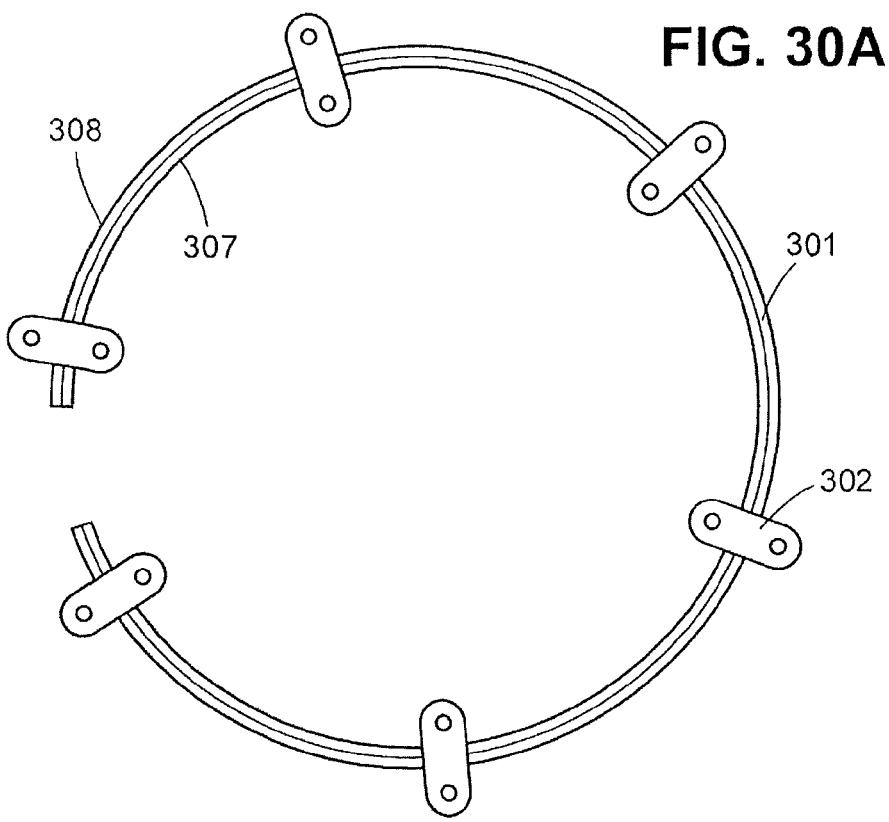
FIG. 30A
FIG. 30B
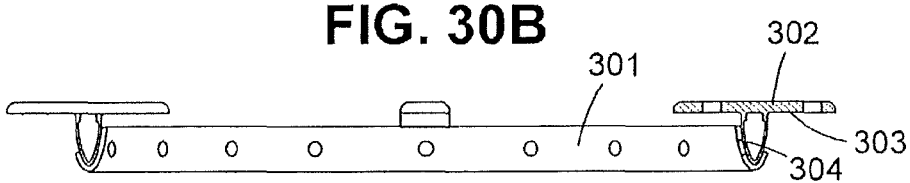

CRANIOTOMY CLOSURES AND PLUGS

CROSS REFERENCE TO RELATED APPLICATION

This application is a Continuation of U.S. patent application Ser. No. 11/333,102 filed Jan. 17, 2006 now U.S. Pat. No. 7,833,253, of the same title, the entire disclosure of which is incorporated herein by reference.

FIELD OF THE INVENTION

The invention relates to surgical strip fasteners, particularly for use in reattaching a skull flap removed during brain surgery, and methods of reattaching the skull flap using the strip fasteners. The invention also has to do with cranial plugs used to fill small openings in the cranium or the burr holes made to facilitate cutting out a skull flap. In a further aspect, the invention relates to surgical strip fasteners and cranial plugs and methods which enhance bone growth and the consequent healing of the skull flap and the skull.

BACKGROUND OF THE INVENTION

Surgical access to the brain for neurosurgical procedures is created by removing a portion of the patient's skull, a procedure termed a craniotomy. The craniotomy is determined by the location of the pathology within the brain, the safest/easiest access route and the degree of exposure required for the procedure. Once the location is determined, the first step is to create an initial perforation of the full thickness of the skull. Special skull perforators are available to create perfectly round holes but most surgeons simply use a rounded, end-cutting burr to create the perforation. Typically the perforation is in the range of about 11-15 millimeters (mm) in diameter. A surgeon may choose to create more than one perforation around the perimeter of the planned craniotomy. Some surgeons prefer a single perforation and others use more than one, but there is no standard number. Once this hole is created, it allows the insertion of a rotary powered surgical instrument (e.g., a craniotome) which is used to create a continuous cut (kerf) around the perimeter of the craniotomy. This kerf begins and ends at the perforation when there is one perforation or it runs from one perforation to another when more than one perforation is made in the skull. The kerf is made with a side cutting burr which is shielded from the dura (outer covering of the brain) by a foot plate on the craniotome. The foot plate extends below and forward of the cutting burr and the surgeon keeps the tip of the foot plate in contact with the inner surface of the skull as he performs the craniotomy. The typical kerf is made freehand with an approximately 2 mm diameter burr. The shape of the craniotomy is therefore highly variable and the kerf is not always oriented perpendicular to the skull. The kerf may be larger than 2 mm in some areas as well. Over the course of the kerf, the skull thickness will vary, typically over the range of 3-8 mm in adults.

Once the cut is complete, the skull flap is removed from the skull and placed on the sterile back table for reinsertion at the end of the procedure. After completion of the soft tissue surgery (typically 1-6 hours), the skull flap is inserted back into the craniotomy and fixated to prevent movement and restore the original contour of the skull. The surgeon may bias the skull flap toward one side or another to create bone-to-bone contact in a particular area or he may leave a gap around the entire flap. The scalp is then closed and the patient is sent to the neurosurgical intensive care unit for recovery.

If complications develop while the patient is in the hospital, there may be the need for emergency access to the brain through the craniotomy site. In addition, some patients may return for subsequent craniotomies in the same region, particularly in cases of recurrent tumors. Postoperative imaging studies (MRI or CT) are generally conducted on all patients. There is no clear evidence that the skull flap ever completely heals (solid bony union) in adults. It is more likely that a combination of new bone formation and fibrous connective tissue fills the gap between the skull and the skull flap.

From a surgeon's perspective, the method of reattaching the bone flap must be safe, simple to use, be rapidly applied, permit emergent re-entry, not interfere with postoperative imaging studies, provide stable fixation and have an acceptably low profile. The ideal method would result in complete fusion of the bone flap to the native skull with no long term evidence of prior surgery.

Current methods of reattaching the skull flap include drilling a series of small holes in the edge of the skull and the edge of the flap. Sutures are then passed through the corresponding holes and the flap is secured back into the skull opening from which it was taken. Because the fit is not exact due to the material removed by the craniotome, the flap can sag and sit slightly below the surface of the skull resulting in a depressed area that is obvious through the skin.

Another common reattachment method substitutes stainless steel wire for the suture material and fewer holes are used. There is still the risk of a cosmetically objectionable depressed area resulting. Metallic cranial fixation is (generally) only ever removed if it becomes symptomatic or if it interferes with subsequent surgeries.

More recently, surgeons have begun to use the titanium micro plates and screws that were developed for internal fixation of facial and finger bones. While this method results in a more stable and cosmetic result, it is relatively expensive, does not insure fusion and leaves foreign bodies at the surgical site.

All of these methods take ten minutes to one hour of additional surgery after the soft tissue (brain) surgery.

There is another method in which a titanium rivet (or clamp) is placed inside the skull with the stem of the rivet (clamp) passing between the skull and the flap. A large "pop rivet" type tool is used to force an upper titanium button down over the stem of the rivet, locking the flap and the skull in place between the upper and lower buttons. Three or four of these rivets and buttons are used to secure the flap in place. This method can be faster than other methods and less expensive than the titanium plates, but more expensive than sutures or wires. Just as with titanium plates and screws, fusion is not assured and foreign bodies remain in the patient.

According to the present invention we have developed new surgical strip fasteners and cranial plugs for, and methods of, reattaching a skull flap in a skull opening. The fixation provided utilizing a strip fastener and cranial plugs and practicing the methods of the invention is secure and cosmetically acceptable. The strip fastener and plugs also can enhance bone growth in a manner which causes healing by means of bone-to-bone reattachment of the skull flap to the skull.

SUMMARY OF THE INVENTION

The surgical strip fasteners of the present invention are sufficiently flexible that they can be shaped to follow the perimeter contour of the skull flap and, consequently, the perimeter contour of the opening in the skull from which the flap was removed. This allows the surgeon to reattach the flap in generally the same position from which it was removed, thereby maintaining the contour of the skull in a manner which is cosmetically desirable.

A strip or ribbon of material comprises the element of the strip fastener which is shaped to follow the perimeter contour of the skull flap. In most embodiments the strip fastener is provided with tabs or flanges which are disposed over and adjacent to the skull flap and the skull. The strip fastener also can be provided with one or more cavities disposed along its length. The cavities generally are located in the strip fastener so that they are disposed between the skull flap and the skull when the strip fastener is implanted in a patient. For example, the cavity may have a uniform cross section along the entire length of the strip fastener such as in the shape of a U, V, J, W or pleats or corrugations or it may be a closed tube having the cross-sectional shape of a circle, oval, ellipse, square, rectangle, triangle or any other closed geometric shape. The outer width of these cross-sections is sometimes referred to herein as the outer width of the channel. References to such strip shapes herein each refer to the shape of a cross-section taken transverse to the length of the strip fastener. In other embodiments one or more tubular elements are disposed on the underside of the strip fastener and these are disposed between the skull flap and the skull when the strip fastener is implanted in a patient.

The surgical strip fasteners, including those with cavities or tubular elements, have side portions which are disposed between the skull flap and the skull when the strip fastener is implanted. These side portions can have openings such as holes, slits or lateral slots which permit bone regrowth or these openings can be used to secure the strip to the edge of either the skull flap or skull by means of adhesives, glues, screws, tacks, staples, etc. Additionally the slits may be oriented along a transverse axis through one sidewall and a portion of the bottom section of the strip, allowing the strip additional flexibility. The cavities also have a bottom portion and the tubular elements have bottom and top portions and these bottom and/or top portions also can have openings such as holes or lateral slots.

As a further option the cavities or tubular elements can be filled or partially filled with medication, bone paste, bone growth enhancers and the like.

The cranial plugs of the invention are used to plug small circular openings in the skull such as those made by a surgeon to gain access for surgery or to insert a cutting instrument such as a craniotome to cut out a skull flap. Sometimes more than one small hole is made in the skull to facilitate cutting out a skull flap and, following surgery, the cranial plugs can be used to fill each of those holes, sometimes referred to as burr holes. The cranial plugs can be used by themselves, in combination with the strip fasteners of the invention or in combination with other fasteners. Some of the cranial plug designs also can be filled or partially filled with medication, bone paste, bone growth enhancers and the like.

Other variations and embodiments are described in more detail below and in the drawings and further variations will be apparent to those skilled in the art based upon the principles of the invention set forth herein.

BRIEF DESCRIPTION OF THE DRAWINGS

The appended drawings are not intended to illustrate every embodiment of the invention but they are representative of embodiments within the principles of the invention. The drawings are for illustrative purposes and are not drawn to scale.

In FIG. 8C the tubular strip has a helical slit along its length.

FIG. 12C is an expanded view of the FIG. 12 embodiment and FIG. 12D is a section view of the FIG. 12 embodiment in a use condition.

FIG. 13 is a perspective view of a cranial plug which can be snap-fit or inserted with a compression tool and FIGS. 13A, and 13B-13C are top views and section views, respectively of the FIG. 13 embodiment.

FIG. 18 is a perspective view of a cranial plug with two legs which can be inserted after any of the strip fasteners with tabs have been implanted. It straddles the strip and covers the burr hole. FIGS. 18A, and 18B-18C are a top view and section views, respectively, of the FIG. 18 embodiment.

FIG. 30 is a perspective view of a strip fastener of the invention having a perforated, J-shaped, flexible strip. FIG. 30A is a top view and FIG. 30B is a section view of the FIG. 30 embodiment.

DESCRIPTION OF THE PREFERRED EMBODIMENTS

Figure 1:
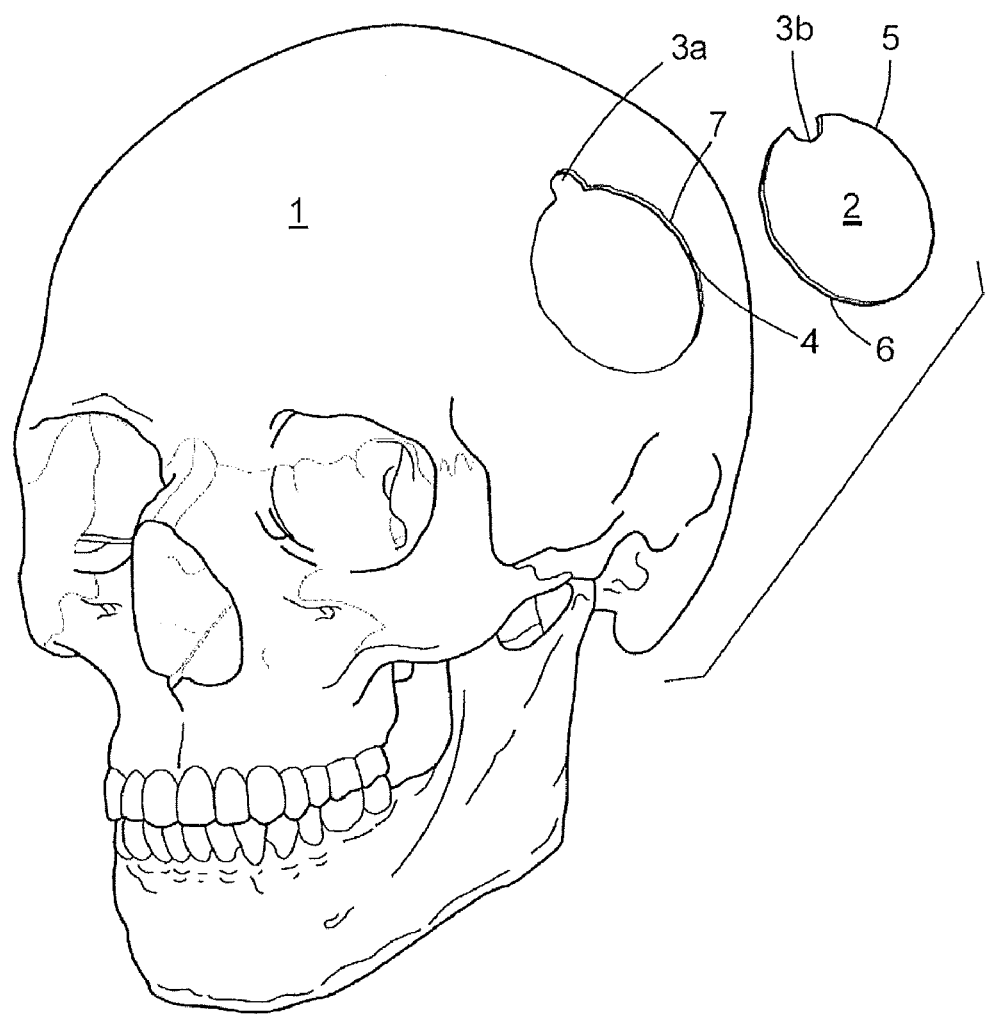
FIG. 1 is a representative view of a human skull showing one possible location and configuration of a craniotomy skull flap.

For reference, a human skull 1 with a craniotomy skull flap 2 is shown in FIG. 1. The skull flap 2 is defined by a burr hole 3 and the connecting osteotomy cut 4, wherein the skull portion of the burr hole is designated in FIG. 1 as 3a and the skull flap as 3b. The skull flap 2 has a perimeter contour 5 but it need not be of the particular shape shown and may have any number of burr holes 3. (See FIG. 15 for a 3 burr hole configuration.) On the opposing sides of the osteotomy cut 4 is the respective bone edge surface 6 of the skull flap 2 and the surrounding bone 7 of the skull 1, respectively. The bone edge surface 6 has a perimeter contour 5 generally matching the contour of the surrounding bone 7 of skull 1.

Figure 1A:
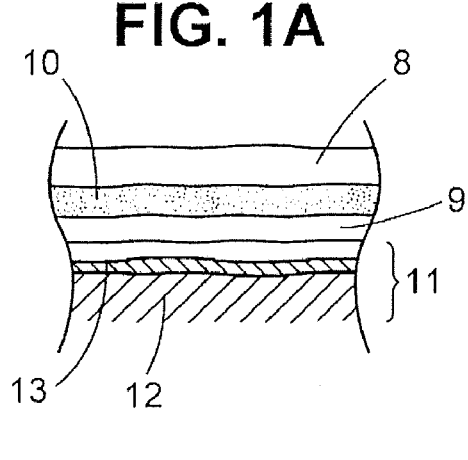
FIGS. 1A and 1B are section views of portions of skull bone and cranial cavity.
Figure 1B:
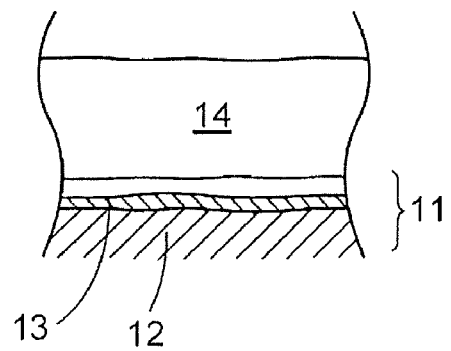

The skull 1 and skull flap 2 are either made from bone that has a three layer composition, as shown in FIG. 1A, or a single layer as shown in FIG. 1B. Referring to FIG. 1A, the outermost layer is the outer cortical bone 8 and the innermost layer is the inner cortical bone 9. Between these two stiff layers is a relatively soft middle layer of cancellous bone known as the diploe 10. Interior to the inner cortical bone 9 is the cranial cavity 11 housing the brain 12 and its surrounding dura matter 13. FIG. 1B illustrates the condition wherein the skull bone is comprised entirely of cortical bone 14.

The present invention is particularly adapted for securing a craniotomy skull flap 2 to the skull 1, but may be used in other situations where appropriate. The present illustrative discussion assumes that a strip fastener of the invention is being used to close a craniotomy skull flap 2 having one burr hole 3 but the same principles apply if the surgeon makes more than one burr hole in order to open up the skull for surgery. The osteotomy cut 4 may be normal to the surface of the skull 1 or at an angle thereto.

The term "strip fastener" is used herein to mean a surgical strip fastener of the invention and the term "plug" is used to mean a cranial plug (sometimes alternatively designated as a cranial perforation closure) of the invention.

The strip fasteners of the invention can be made straight or with a precurvature to reduce kinking when they are shaped to follow the perimeter contour of the skull flap.

The strip fasteners and plugs of the invention can be made of various biocompatible materials and combinations of biocompatible materials. Suitable materials include tissue friendly metals, alloys, plastics and reinforced plastics which are commonly used in surgical implants of all kinds. Such materials include materials that have sufficient strength and flexibility to meet the objectives of the invention. The materials also can optionally be porous, semi-porous or semi-permeable. Many of the materials that have been approved by the United States Food and Drug Administration (FDA) for surgical implant applications are also suitable.

Generally speaking, there are three main types of alloys used in biocompatible metals today, titanium alloys, cobalt alloys and stainless steel alloys. An exhaustive list is available on the FDA website which also provides the reference numbers and effective dates of the ASTM or ISO standards for many of the materials that are suitable. Some examples include unalloyed titanium and titanium alloyed with aluminum, niobium and/or vanadium; stainless steel and other irons alloyed with molybdenum, chromium, cobalt, tungsten, aluminum, nickel, manganese or vanadium in various combinations, various other stainless steels and other iron alloys, for example, with aluminum oxides, zirconium oxides, tantalum and calcium phosphates. This list is not intended to be exhaustive.

Numerous types of high strength polymers also are employed to make implants and many of these are identified not only on the FDA website mentioned above but also on the ASTM website. Examples of suitable high strength polymers include polyetheretherketone (PEEK), epoxys, polyurethanes, polyesters, polyethylenes, vinyl chlorides, polysulfones, polytetrafluoro-ethylene (PTFE), polycarbonates, polyaryletherketone (PAEK), polyoxymethylene, nylon, carbon fiber polyester, polyetherketoneetherketoneketone (PEKEKK), silicones, hydrogels and the like. When a polymer is used, a small wire or other radiopaque material can be incorporated in the main body of the base for purposes of x-ray detection.

The foregoing lists of materials may have application in some embodiments of the present invention but not in others as will be apparent to those skilled in the art based on requirements of strength, flexibility, machinability and the like for the particular application. The lists are intended to be illustrative and not exhaustive. Other materials and new materials may be employed based upon the principles of the invention as set forth herein.

For purposes of this specification, the term "high strength polymer(s)" is defined as any tissue-friendly non-bioabsorbable polymer, copolymer, polymer mixture, plastic or polymer alloy having sufficient strength to withstand without failure the stresses that a fastener of the invention would normally be subjected to during surgery or in the body.

Bioabsorbable material can also be used to make all or a portion of one or more of the component parts of the strip fasteners or plugs of the invention and/or the bioabsorbable material can be applied as a partial or complete coating on such component parts.

The term "bioabsorbable material" as used herein includes materials which are partially or completely bioabsorbable in the body.

Suitable bioabsorbable materials include collagen, polyglycolide, poly(lactic acid), copolymers of lactic acid and glycolic acid, poly-L-lactide, poly-L-lactate; crystalline plastics such as those disclosed in U.S. Pat. No. 6,632,503 which is incorporated herein by reference; bioabsorbable polymers, copolymers or polymer alloys that are self-reinforced and contain ceramic particles or reinforcement fibers such as those described in U.S. Pat. No. 6,406,498 which is incorporated herein by reference; bioresorbable polymers and blends thereof such as described in U.S. Pat. No. 6,583,232 which is incorporated herein by reference; copolymers of polyethylene glycol and polybutylene terephthalate, and the like. The foregoing list is not intended to be exhaustive. Other bioabsorbable materials can be used based upon the principles of the invention as set forth herein. Some of the most common:

| | |
|---|---|
| Poly-L-lactic acid (PLLA) | Poly-DL-lactic acid (PDLLA) |
| Polyglycolic acid (PGA) | Polydioxanone (PDS) |
| Polyorthoester (POE) | Poly-C-capralactone (PCL) |

Bioactive materials can be admixed with the bioabsorbable materials, impregnated in the bioabsorbable materials and/or coated on the outer surface thereof. Bioactive materials, including natural and/or synthetic materials, also can be used to fill cavities in the strip fasteners or cranial plugs. These materials can include, for example, bioactive ceramic particles, bone chips or paste, platelet rich plasma (PRP), polymer chips, synthetic bone cement, autologous materials, allograft, cadaveric materials, xenograft, nanoparticles, nanoemulsions and other materials employing nanotechnology, capsules or reinforcement fibers. And they can contain, for example, antimicrobial fatty acids and related coating materials such as those described in Published U.S. Patent Application No. 2004/0153125 A1; antibiotics and antibacterial compositions; immunostimulating agents; tissue or bone growth enhancers and other active ingredients and pharmaceutical materials known in the art.

The products of the invention which are made with bioabsorbable material can be made by molding, extrusion, heat shrinking or coating the bioabsorbable material on a base which has been provided with attachment means such as those described in our pending patent application Ser. No. 11/025,213 filed Dec. 29, 2004 which is incorporated herein by reference. Some of the screws and other fastening devices described in our pending patent application Ser. No. 11/025,213 filed Dec. 29, 2004 can also be used in or in combination with the strip fasteners and cranial plugs of the present invention. When the bioabsorbable material will have functional mechanical properties which are not made from the base material, the bioabsorbable material can be molded onto the base in the desired shape. Alternatively, the bioabsorbable material also can be coated, shrink wrapped or molded onto the base. If necessary, the bioabsorbable material can be machined to the desired shape and/or dimensions.

As will be apparent to those skilled in the art, the sizes of the strip fasteners and plugs of the invention can be varied to meet their intended applications. The shapes can take various forms in addition to those illustrated without deviating from the principles of the invention. And the sizes, lengths and widths can be varied for particular applications within the principles of the invention set forth herein.

Various methods can be used to employ the strip fasteners and/or cranial plugs of the invention as will be apparent to those skilled in the art based upon the embodiment(s) of the fasteners and/or plugs selected for use by the practitioner. For example, the strip fastener may be attached to the skull flap first, then the skull flap and strip would be positioned in the skull opening and the strip fastener would then be attached to the skull. This would be followed by affixing one or more cranial plugs in the burr hole or holes as needed. In most embodiments antibiotics, bone growth enhancers or other materials disclosed herein could be added in cavities in the strip fastener and/or plugs before or after the skull flap is reattached to the skull, as will be apparent to those having ordinary skill in the art. Another method would be to reattach the skull flap using the cranial plugs followed by attachment of the strip fastener(s). In situations where three or more burr holes are created, the surgeon could choose to install a plug in each partial burr hole in the flap, affixing the flanges or the side sections of the plug to the top surface of the flap or edge of the flap respectively. The flap with the affixed plugs could then be inserted back into the skull and the plugs could provide a "snap-fit" or "press-fit" in their respective burr holes and/or the flanges could be affixed to the top surface of the skull. In such situations, the surgeon may choose not to use strips in addition to the plugs. It should be noted that the term "affixing" as used herein includes "snap-fit" and "press-fit" as well as the other means such as screws, staples, tacks, adhesives and the like described herein. In still another method, the cranial plugs can hold the strip fasteners in place while reattaching the skull flap or can be used in conjunction with strips to fixate the flap. Other methods will be apparent to those having skill in the art depending upon the type of strip fastener(s) or plug(s) selected by the practitioner, the characteristics of the skull and/or skull flap, the type of surgery involved and the likelihood or unlikelihood of the need to re-open the surgical site.

Figure 19:
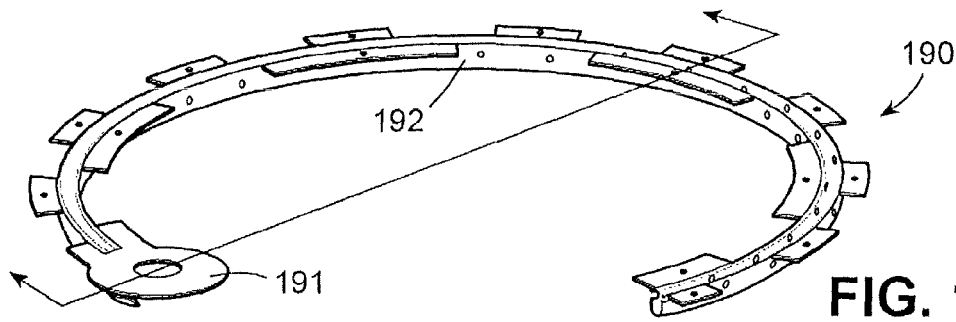
FIG. 19 is a perspective view of a combination of a plug and a strip fastener. The two are combined into a single implant.
Figure 19A:
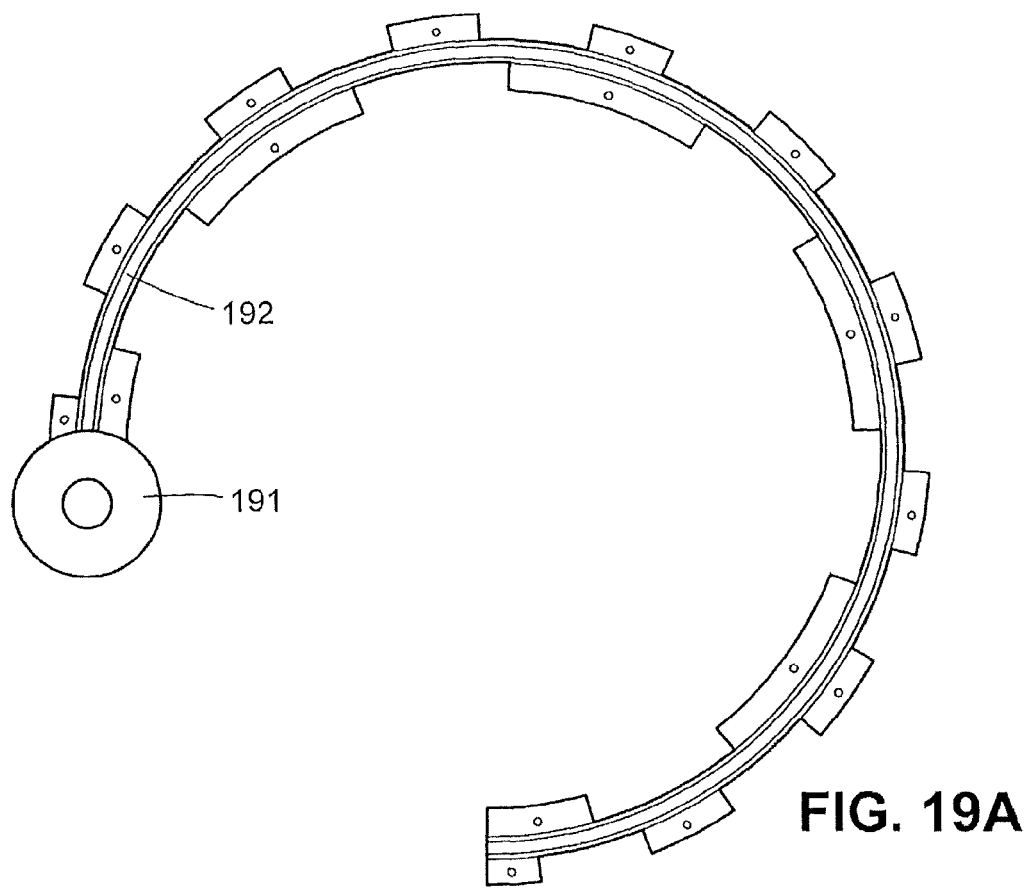
FIGS. 19A and 19B are a top view and a section view of the FIG. 19 embodiment.
Figure 19B:
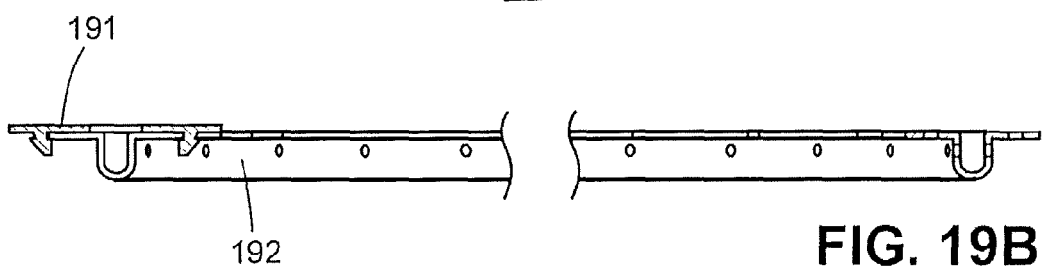

As noted above, the strip fasteners of the invention can be formed around the perimeter contour of the skull flap and attached to the skull flap before attachment to the skull. The step of attaching the fastener to the skull flap can be done by operating room personnel while the surgeon is performing surgery. This saves substantial time when the skull flap is reattached following surgery. The previously attached strip fasteners support the skull flap and insure that the top of the flap coincides with the top surface of the skull. When cranial plugs are used in combination with the strip fasteners, they can be installed before or after the skull flap has been reattached to the skull. If more than one burr hole is used to make the cranial flap, the strip fastener may be cut and attached in sections to the skull flap to leave room for a cranial plug at each burr hole. Alternately the strip portion of the strip fastener may be threaded through one or more cranial plugs prior to attachment to the skull flap and the strip fastener may be essentially continuous around the entire kerf. Another option would be to use a combined strip fastener and plug implant as shown in FIG. 19, particularly in cases where only a single burr hole is created. As noted above, the shape of the skull flap is highly variable and when it is reattached to the skull it is positioned in a manner to match the position from which it was removed, similar to replacing a piece of a jigsaw puzzle.

There are numerous suitable options for fastening the strip fasteners of the invention to the skull flap and the skull. These include screws, staples, tacks, glues, adhesives, peel off adhesives, press-fit, snap-fit and combinations of two or more thereof. For example, a strip fastener may be stapled onto the skull flap and then press-fit into the opening in the skull. These fastening methods may be used to affix the strips and plugs to any contacting surface of either the skull flap or skull. In some cases it might be preferable to secure the tabs of the strips or the flanges of the plugs to the top surfaces of the skull or skull flap. In other instances the surgeon may choose to affix the sidewall of the strip or plug to the respective edges of the skull or skull flap.

Figure 2:
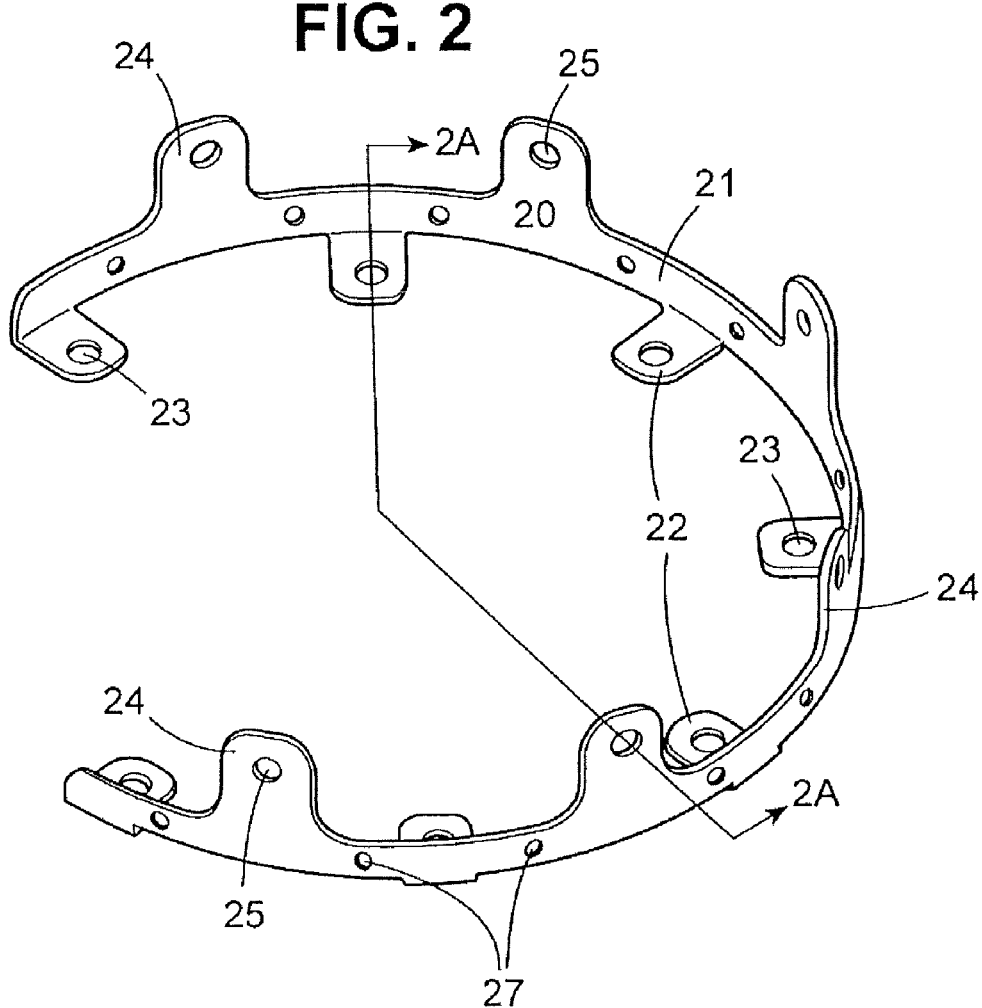
FIG. 2 is a perspective view of one embodiment of a strip fastener of the present invention in a pre-use state and FIG. 2A is a section view of the FIG. 2 embodiment.
Figure 2A:
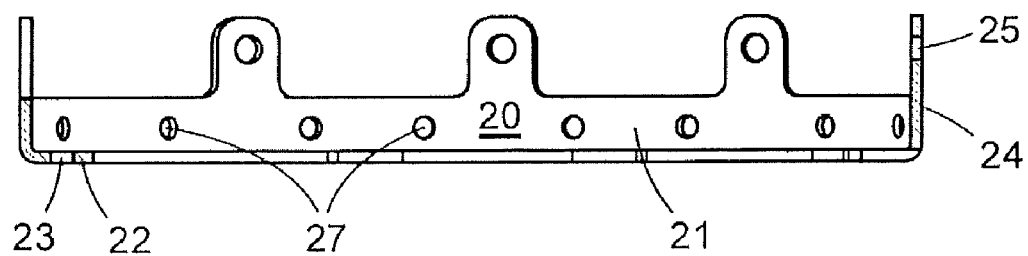
Figure 2B:
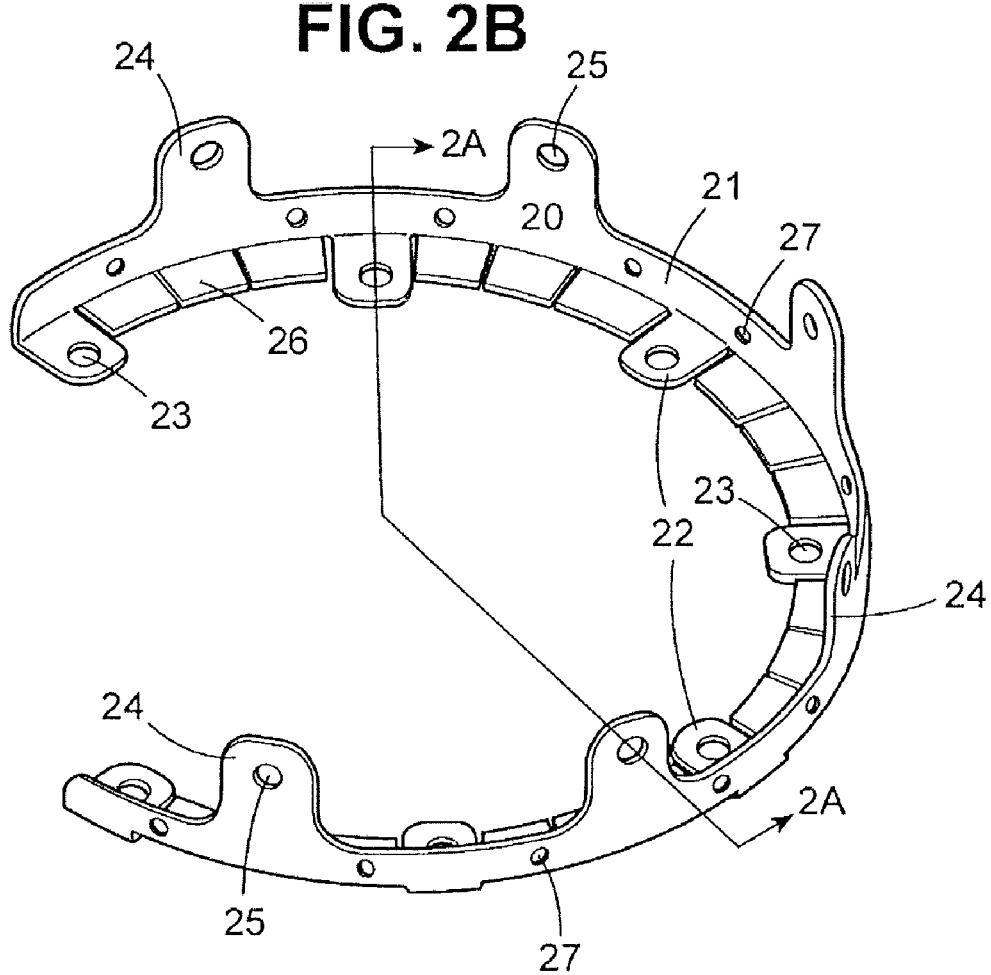
FIG. 2B is a perspective view of variant of the FIG. 2 embodiment and FIG. 2C is a section view of the FIG. 2B embodiment.
Figure 2C:
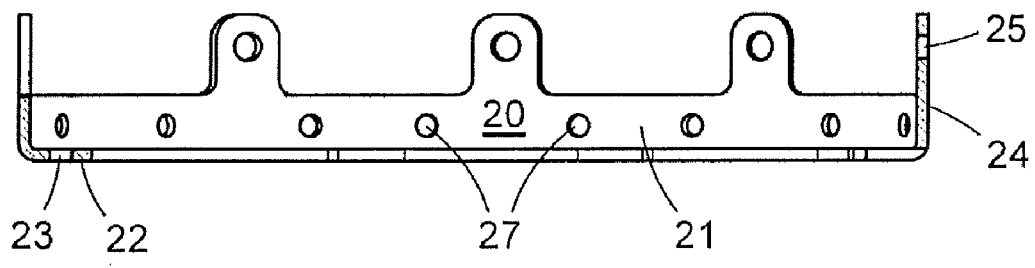
Figure 8:
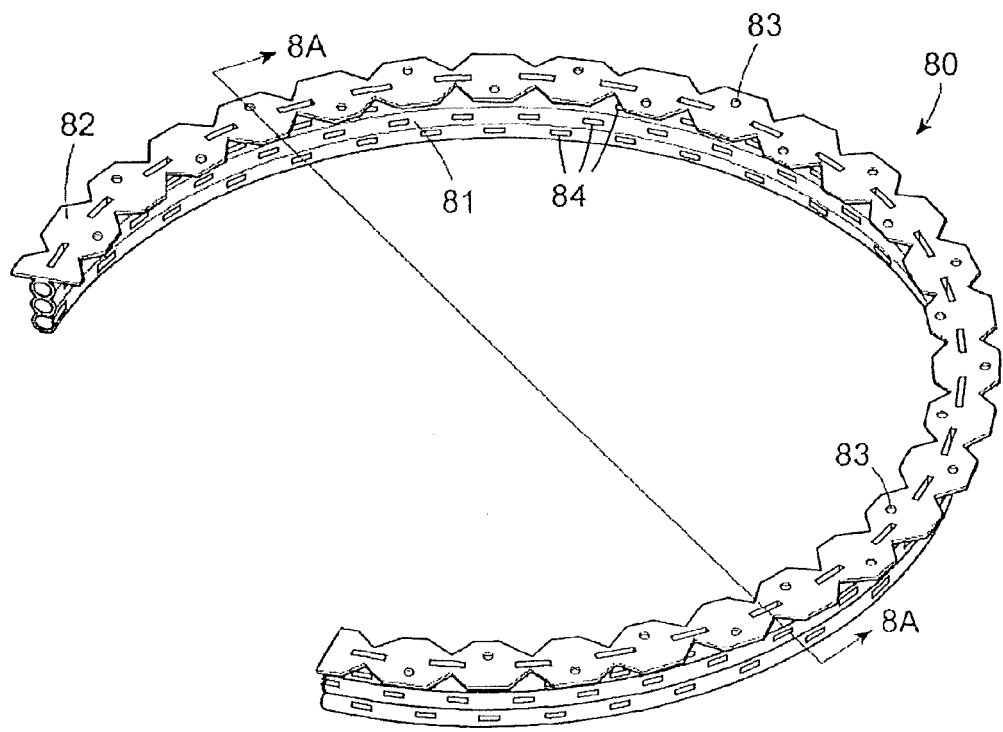
FIG. 8 is a perspective view of a strip fastener of the invention having a flexible strip comprised of three stacked tubes and FIG. 8A is a section view of the FIG. 8 embodiment.
Figure 8A:
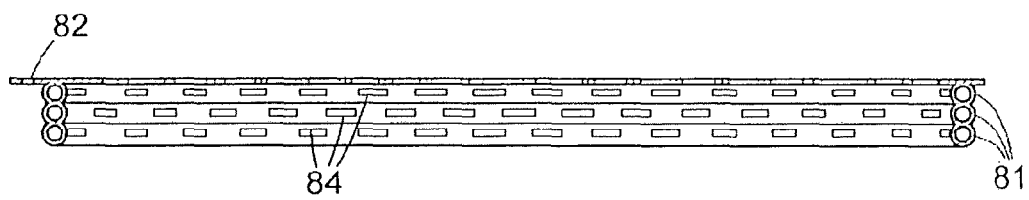

For the embodiment illustrated in FIGS. 2 and 2A, the strip fastener 20 is comprised of a strip 21 which is pre-curved and sufficiently flexible to be shaped to follow the perimeter contour of a skull flap. Flap tabs 22 are disposed on the bottom side of strip 21 and are arranged for attachment to the underside of the skull flap such as by using screws through holes 23 or staples or adhesives or other suitable means known in the art. Skull tabs 24 are for attachment to the outer surface of the skull. When the strip fastener 20 is attached to the skull, tabs 24 are folded outwardly onto the skull outer surface and are fastened either using screws through holes 25 or staples or adhesives or other suitable means known in the art. Strip 21 can optionally be perforated with holes 27 and/or slots (not shown) such as those illustrated in other embodiments of the invention, for example, in FIGS. 5 and 6 or slits (not shown) as illustrated in FIG. 8. When this strip fastener is employed, it can either be attached first to the skull flap or the skull. Of course, if it is attached to the skull first, an adhesive or similar material will be used to attach it to the skull flap. In addition, the cross-section of the strip can be "L" shaped between the inner tabs 23 as illustrated in FIGS. 2B and 2C to provide a "floor" created by tabs 26 for containing the previously mentioned bioactive materials used to fill portions or all of the kerf and promote fusion of the flap to the skull.

Figure 3:
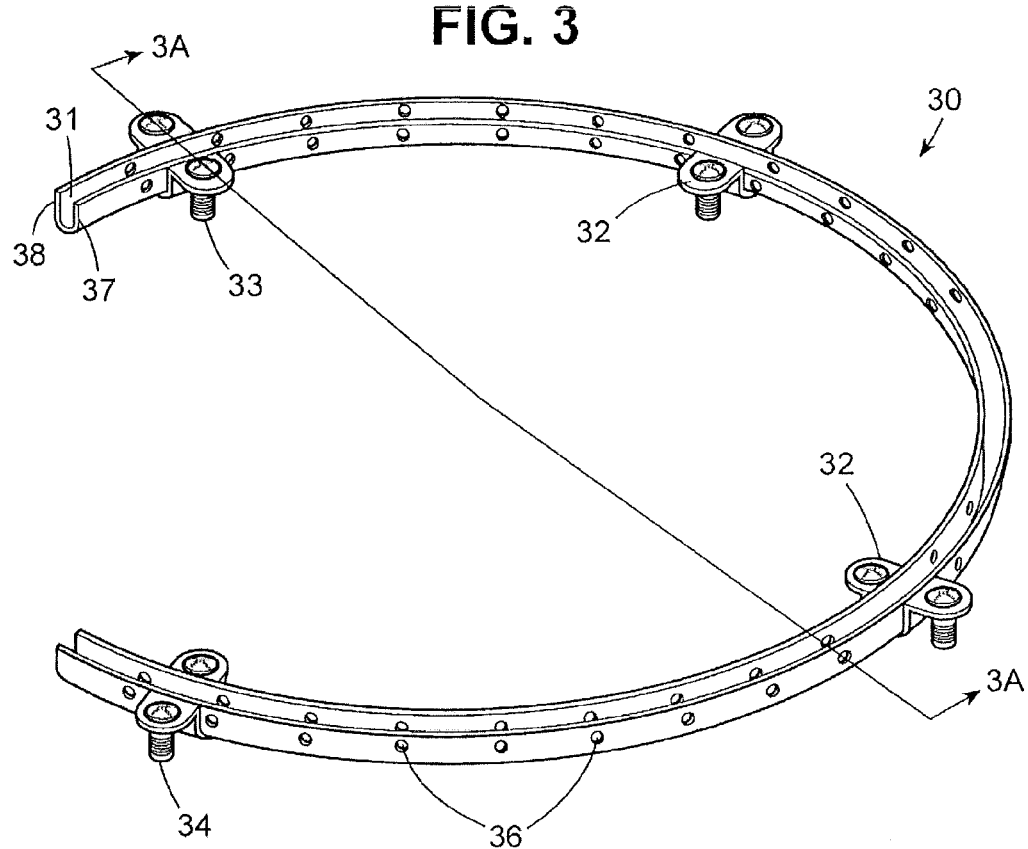
FIG. 3 is a perspective view of an embodiment of a strip fastener of the invention having a perforated, U-shaped, flexible strip and "U-shaped" clips
Figure 3A:
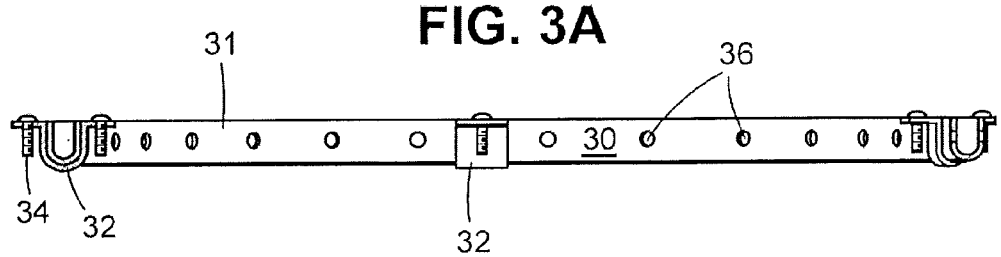
FIG. 3A is a section view of the FIG. 3 embodiment.
Figure 3B:
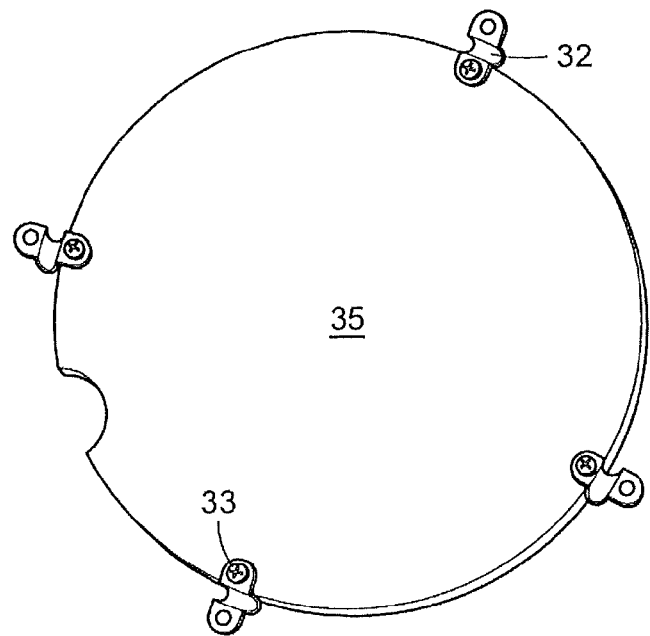
FIGS. 3B, 3C and 3D illustrate a series of steps for reattaching a representative skull flap to a skull using the strip fastener of FIG. 3.
Figure 3C:
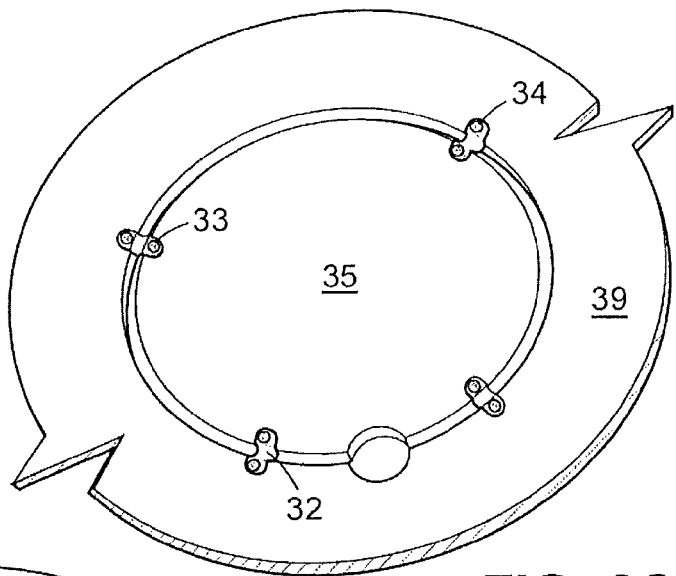
Figure 3D:
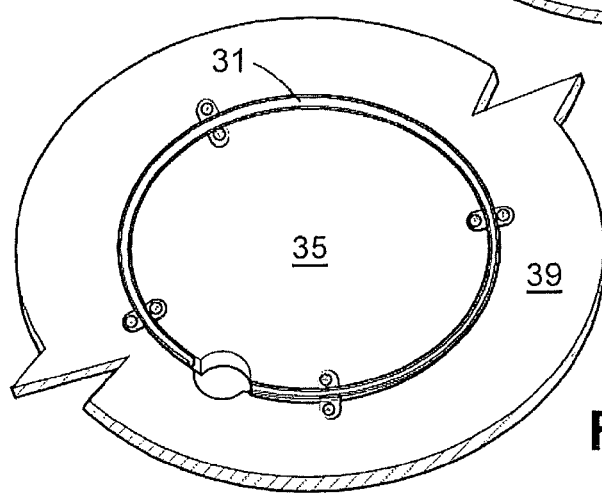

FIGS. 3 and 3A illustrate a strip fastener 30 comprised of a U-shaped strip 31 which is pre-curved and sufficiently flexible to be shaped to follow the perimeter contour of a skull flap. Brackets 32 may be adhered to the strip fastener 30 by adhesives, spot welding or other means suitable for the materials of which the strip 31 and brackets 32 are comprised or they may be only movably retained and able to slide along the length of the strip 31. In another embodiment they may be separate items, composed of the same or different material as the strip 31. In this case they would allow the surgeon the option, for example, of attaching only the brackets to the skull flap before it is replaced into the skull opening as illustrated in FIG. 3B. As illustrated in FIG. 3C, flap screws 33 and skull screws 34, adhesive or other means are used to attach the brackets 32 to the outer surfaces of the skull flap 35 and the skull 39, or alternately to the edges of the skull or skull flap. Following the step illustrated in FIG. 3C, the strip 31 is inserted as shown in FIG. 3D. It is also conceivable that there may be circumstances where the skull flap with attached fasteners is a "press fit" into the skull defect and no screws, staples, adhesive, etc. are necessary to attach to the skull. It is understood that these circumstances may be applicable to many of the embodiments of the surgical fasteners of the invention as will be apparent to those having skill in the art, for example, when the outer width of the channel is sized for a press-fit into the kerf.

Multiple holes 36 are disposed around the inside perimeter 37 and the outside perimeter 38 of U-shaped strip 31. The holes 36 permit bone growth for bone to bone reattachment of the skull to the skull flap or they can be used to affix the sidewalls of the strip to the edges of the skull flap. Bone growth can be enhanced by filling the U-shaped strip 31 with known bone growth enhancers and/or other bioactive materials as described above. This can be done before and/or after the strip fastener 30 is implanted in the patient. This concept can be adapted by those skilled in the art to strip fasteners of other cross sections disclosed herein.

Figure 4:
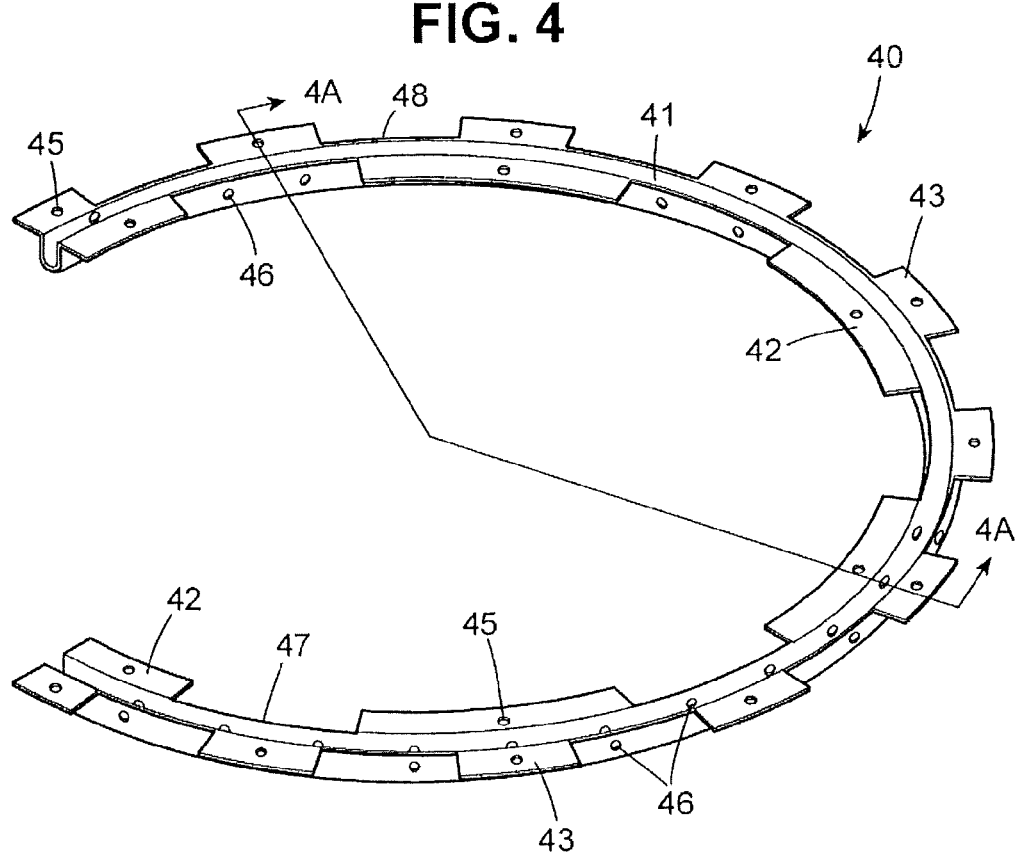
FIG. 4 is a perspective view of another embodiment of a strip fastener of the invention having a perforated, U-shaped, flexible strip
Figure 4A:
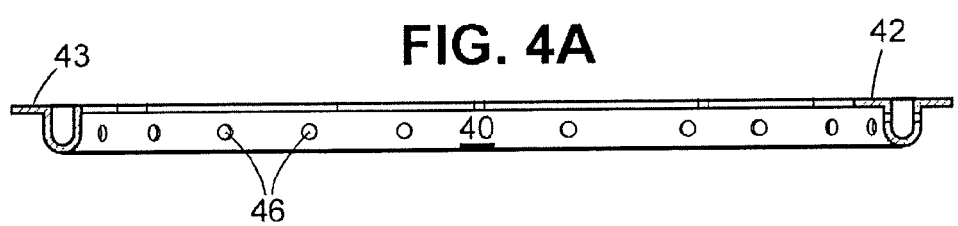
FIG. 4A is a section view of the FIG. 4 embodiment. In this design, the "U-shaped" strip has integral tabs.

The strip fastener 40 illustrated in FIGS. 4 and 4A is a variation of the FIG. 3 embodiment having a U-shaped strip 41 which is pre-curved and sufficiently flexible to be shaped to follow the perimeter contour of a skull flap. Flap tabs 42 and skull tabs 43 are disposed on the open sides of the inside perimeter 47 and outside perimeter 48, respectively, of the U-shaped strip 41. The tabs 42 and 43 are adhered to the skull flap and skull with adhesives, screws, staples or other suitable means known in the art. Multiple holes 46 serve the same function as described in respect of the FIG. 3 embodiment and the U-shaped strip 41 can be filled with known bone growth enhancers and/or other bioactive materials as described above. The outer width of the channel formed by the U-shaped strip 41 is such that it can require some level of compression to seat the flap or it can be sized such that it is slightly thinner than the kerf so that only the tabs contact the skull when the flap is replaced.

Figure 4B:
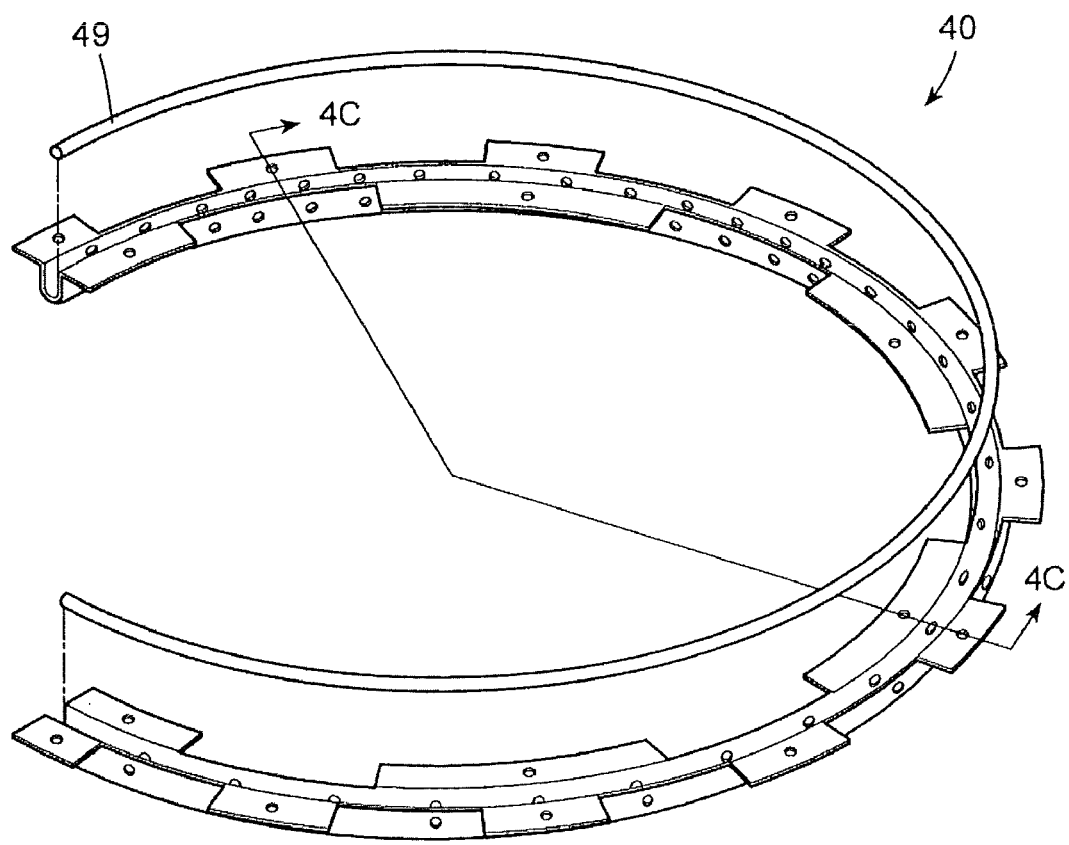
FIGS. 4B and 4C illustrate the FIG. 4 embodiment with an added element for strength and/or drug delivery.
Figure 4C:
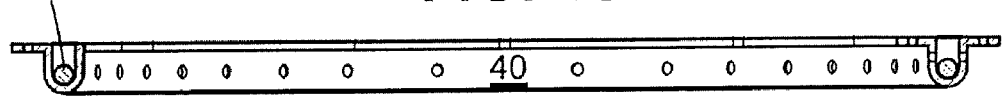

FIGS. 4B and 4C illustrate an added element 49 which can be a strengthening member and/or a tube filled with medication, bioactive materials, bone growth enhancers and the like. Element 49 can be used in combination with several other embodiments of the invention such as the embodiments illustrated in FIGS. 2, 3, 5, 6 (if element 49 is soft and can be pressed in), 7, 9 and 19. Alternatively, element 49 can be used as a bending insert which is used to prevent a flexible strip from springing back or otherwise returning to its original shape as the surgeon contours the strip to the osteotomy cut.

In this alternative embodiment the element 49 can be removed and discarded after the strip fastener is implanted in the patient.

Figure 5:
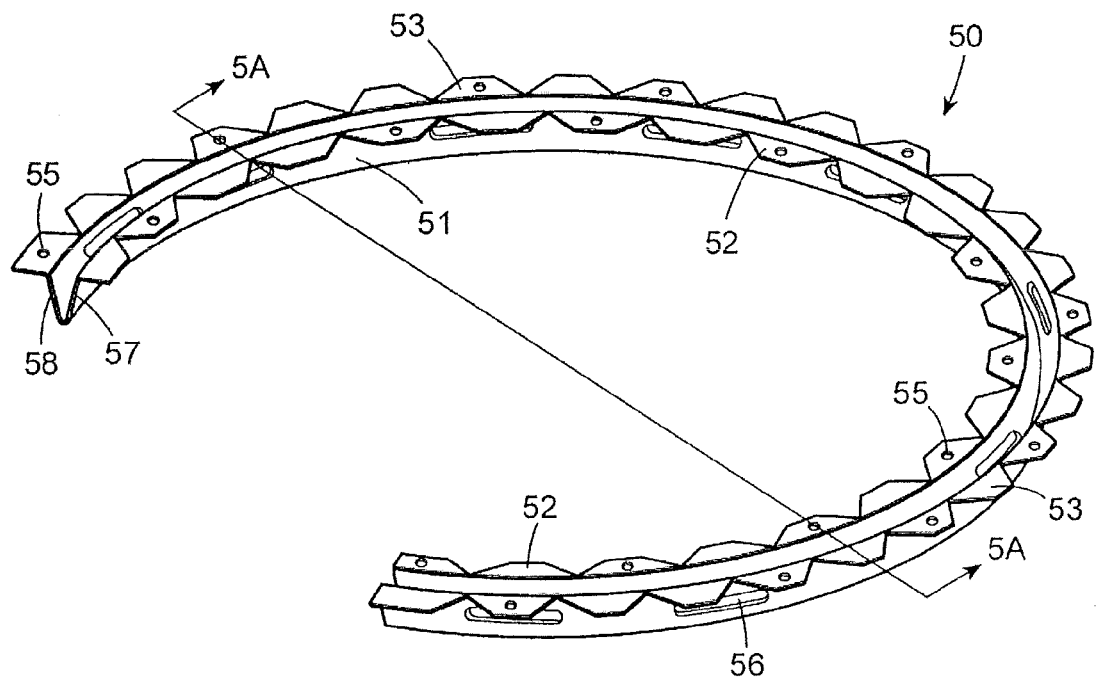
FIG. 5 is a perspective view of an embodiment of a strip fastener of the invention having a V-shaped flexible strip and FIG. 5A is a section view of the FIG. 5 embodiment.
Figure 5A:
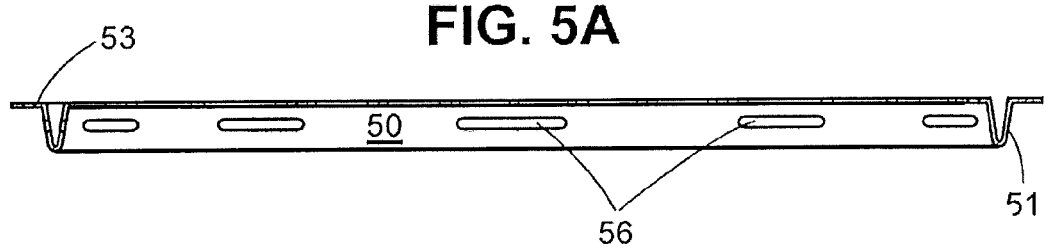
Figure 5B:
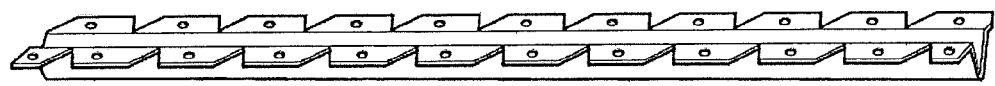
FIG. 5B is a perspective view of the FIG. 5 embodiment which is straight rather than pre-curved.

FIGS. 5 and 5A illustrate a strip fastener 50 comprised of a V-shaped strip 51 which is pre-curved and sufficiently flexible to be shaped to follow the perimeter contour of a skull flap. Flap tabs 52 and skull tabs 53 are disposed on the open sides of the inside perimeter 57 and the outside perimeter 58, respectively, of the V-shaped strip 51. The tabs 52 and 53 can be adhered to the skull flap and skull with adhesive, screws, stapes or other suitable means known in the art or they can be used to locate the strip relative to the top surface of the skull or skull flap if it is affixed through the sidewall to the edge of the skull flap. (This is a common theme of the present invention in respect of the strips and is applicable to many of the plugs as well.) Multiple slots 56 serve the same function as the holes 36 described in respect of the FIG. 3 embodiment and the V-shaped strip 51 can be filled with known bone growth enhancers and/or other bioactive materials and/or medications as described above. FIG. 5B is a perspective view of the FIG. 5 embodiment which has not been pre-curved.

Figure 6:
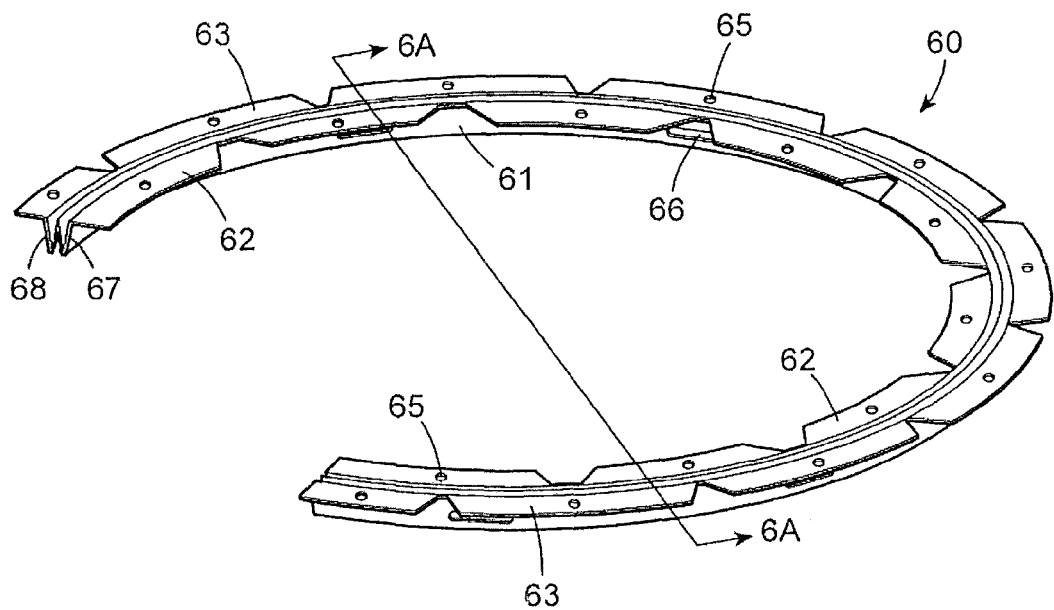
FIG. 6 is a perspective view of an embodiment of a strip fastener of the invention having a W-shaped flexible strip and FIG. 6A is a section view of the FIG. 6 embodiment.
Figure 6A:
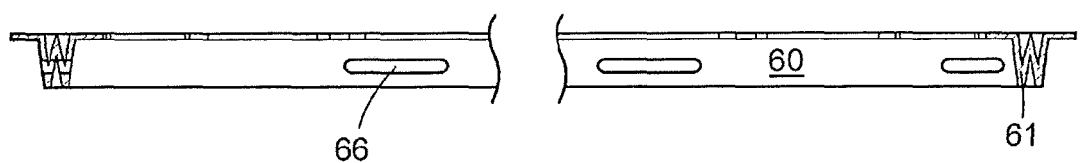

The strip fastener 60 illustrated in FIG. 6 is comprised of a W-shaped strip 61 which is pre-curved and sufficiently flexible to be shaped to follow the perimeter contour of a skull flap. Flap tabs 62 and skull tabs 63 are disposed on the open sides of the inside perimeter 67 and the outside perimeter 68, respectively, of the W-shaped strip 61. The tabs 62 and 63 are adhered to the skull flap and skull with adhesives, screws, staples or other suitable means known in the art. Slots 66 or holes (not shown) can optionally be provided through the W-shaped strip to serve the same functions as described above.

Figure 7:
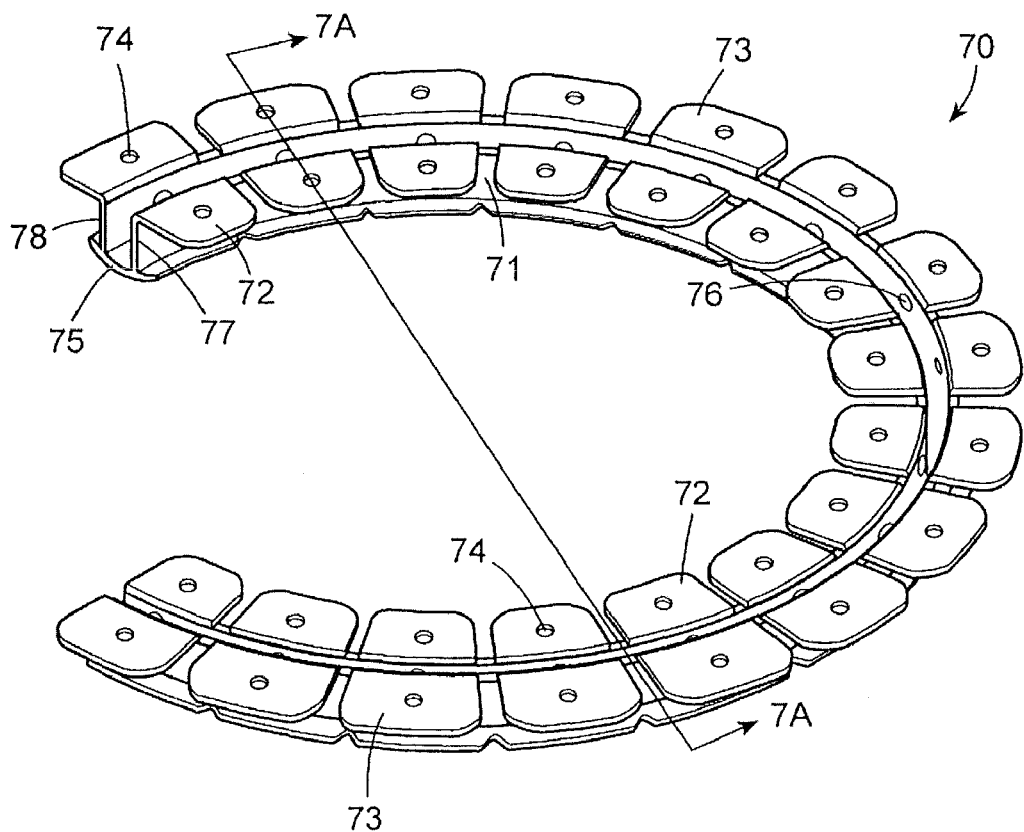
FIG. 7 is a perspective view of an embodiment of a strip fastener of the invention having a compression rib and FIG. 7A is a section view of the FIG. 7 embodiment.
Figure 7A:
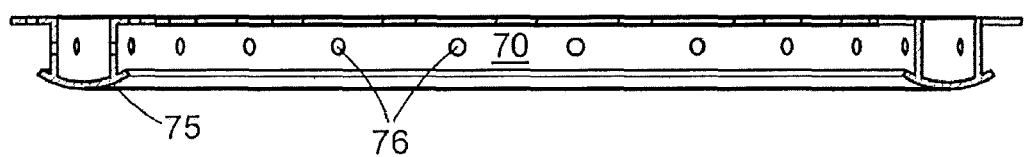

FIG. 7 illustrates a strip fastener 70 comprising a U-shaped strip 71 which is pre-curved and sufficiently flexible to be shaped to follow the perimeter contour of a skull flap. Flap tabs 72 and skull tabs 73 are disposed on the open sides of the inside perimeter 77 and the outside perimeter 78, respectively, of the U-shaped strip 71. A compression rib 75 is disposed on the closed end of the U-shaped strip 71 and multiple holes 76 are disposed around the inside perimeter 77 and outside perimeter 78 of the U-shaped strip 71. In this embodiment the skull flap is first affixed to the strip fastener 70 by means of the tabs, with the compression rib on that side in contact with the skull flap. The skull flap and fastener are then snap fit into place in the skull. Of course, adhesives, screws, staples or other means known in the art can be used to secure the attachment to the skull flap and skull if deemed necessary by the surgeon and optional fastener holes 74 are illustrated to facilitate attachment.

Strip fastener 80 illustrated in FIG. 8 is comprised of one or more flexible tubular strips 81 (three illustrated) which are pre-curved and sufficiently flexible to be shaped to follow the perimeter contour of a skull flap. The term tubular as it is used herein is not meant to restrict the lateral cross-section of the tube to only a circular profile. Oval, elliptical, rectangular or other closed geometric shaped tubular structures (not shown) are also within the meaning of "tubular" and can be used with this design. Tabs 82 are affixed to the tubular strips 81 for attachment to the skull flap and the skull such as by means of adhesives, screws, staples or other means known in the art. Multiple slits 84 or holes or slots (not shown) can optionally be provided in the tubular strips 81 as with many of the other embodiments discussed above. The slits 84 are narrow cuts made through the strips 81. The tubular strips 81 also can be filled with known bone growth enhancers and/or other bioactive materials as described above before the skull flap is reattached to the skull. These tubular strips may be packaged (sterile) with the bioactive materials already filling the cavities. This is also possible for the other configurations but obviously much more practical for a tubular profile.

Figure 8B:
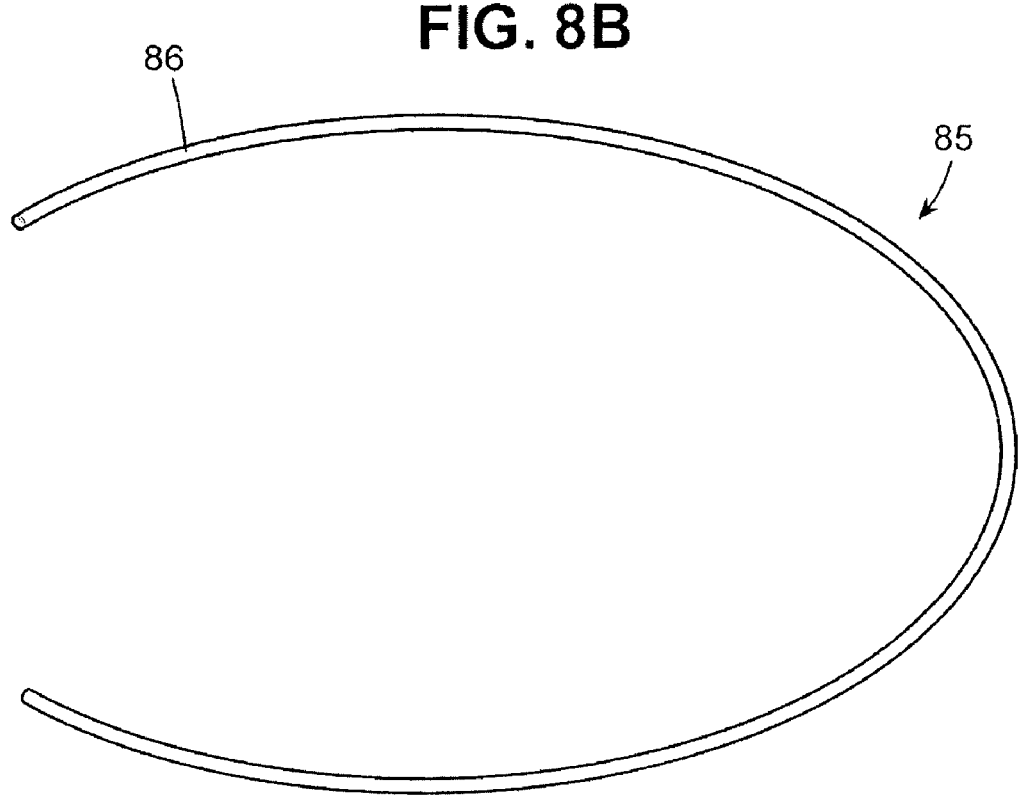
FIGS. 8B and 8C are perspective views of flexible tubular strips which can be used in combination with the brackets 32 of FIG. 3 to make a strip fastener.
Figure 8C:
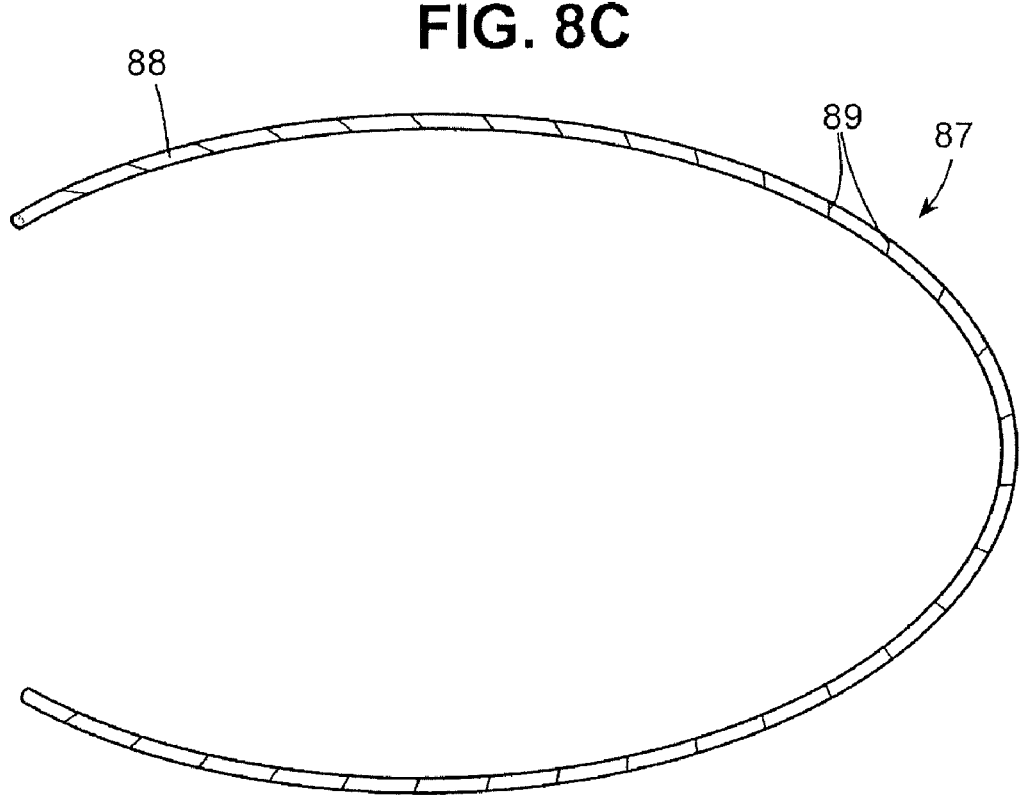

Many of the strip fasteners of the invention can be made without tabs for attachment to the skull flap and skull and instead they can be combined with brackets such as bracket 32 illustrated in FIG. 3. The tubular strip fasteners of FIGS. 8B and 8C are illustrative. As discussed above in respect of the tubular strip fastener of FIG. 8, the tubes of FIGS. 8B and 8C can have various cross sections. In FIG. 8B, tube 86 of strip fastener 85 can be made from a solid, porous, semi-porous or semi-permeable material and/or it can have holes or slots or slits.

Strip fastener 87 in FIG. 8C is comprised of a tube 88 having a helical slit 89 which runs the entire length of the tube.

Multiple tubes of the kind illustrated and described in respect of FIGS. 8B and 8C can be arranged together. For example, they can be stacked as in FIG. 8 or arranged in rows or combinations of rows and stacks or the like. Combinations of tubes 86 and 88 can also be used in such multiple tube embodiments. Tubes may also be made in a rolled form and bone growth enhancers and/or medications can be incorporated into the rolled tubular strip. These rolled strips may be sufficiently flexible (or soft) such that they readily conform to the size and shape of the kerf when inserted in a patient's skull.

Figure 9:
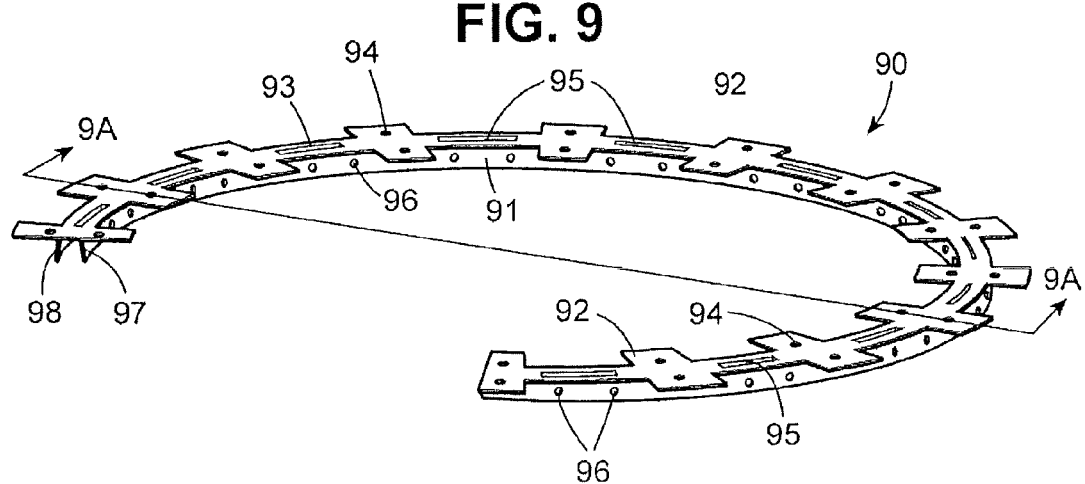
FIG. 9 is a perspective view of a strip fastener of the invention comprising an inverted U-shaped flexible strip and FIG. 9A is a section view of the FIG. 9 embodiment.
Figure 9A:
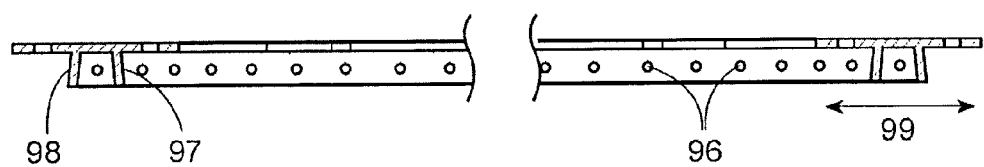

FIG. 9 illustrates a strip fastener 90 comprising an inverted U-shaped strip 91. Closure strip 93 comprising tabs 92 is disposed on the closed end of the U-shaped strip 91 and the strips 91 and 93 are pre-curved and sufficiently flexible to be shaped to follow the perimeter contour of a skull flap. The inside perimeter 97 and outside perimeter 98 are biased outwardly in the directions of arrow 99 so that they can be compressed between the edges of the skull flap and the skull when the skull flap is reattached to the skull. Optional openings 95 are for the introduction of bioactive materials. Optional holes 96 or slits or slots (not shown) can also be disposed around the inside and/or outside perimeters 97 and 98 as discussed above in respect of other embodiments.

Figure 10:
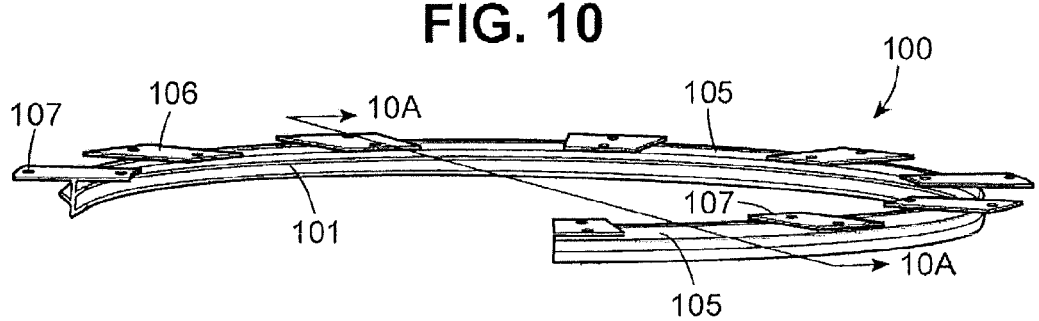
FIG. 10 is a perspective view of a strip fastener of the invention comprising a barbed flexible strip and FIG. 10A is a section view of the FIG. 10 embodiment.
Figure 10A:
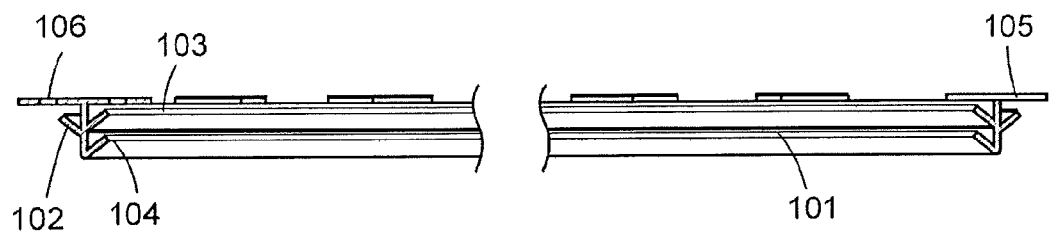

A strip fastener 100 is illustrated in FIG. 10 and it comprises a flexible strip 101 having barbs 102, 103 and 104. Closure strip 105 comprising tabs 106 is disposed on the upper side of flexible strip 101. Holes or slots (not shown) can optionally be provided in strip 101.

Figure 11:
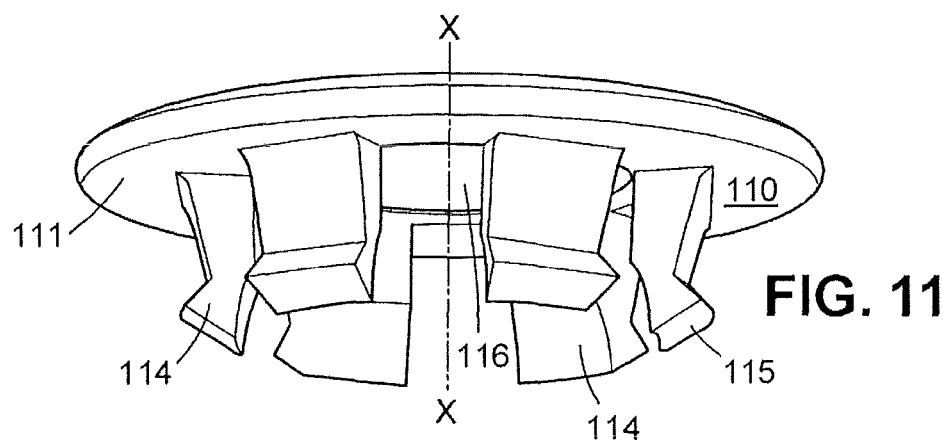
FIG. 11 is a perspective view of a cranial plug of the invention comprising flexible legs for a snap-fit and FIGS. 11A and 11B are a top view and section view, respectively, of the FIG. 11 embodiment.
Figure 11A:
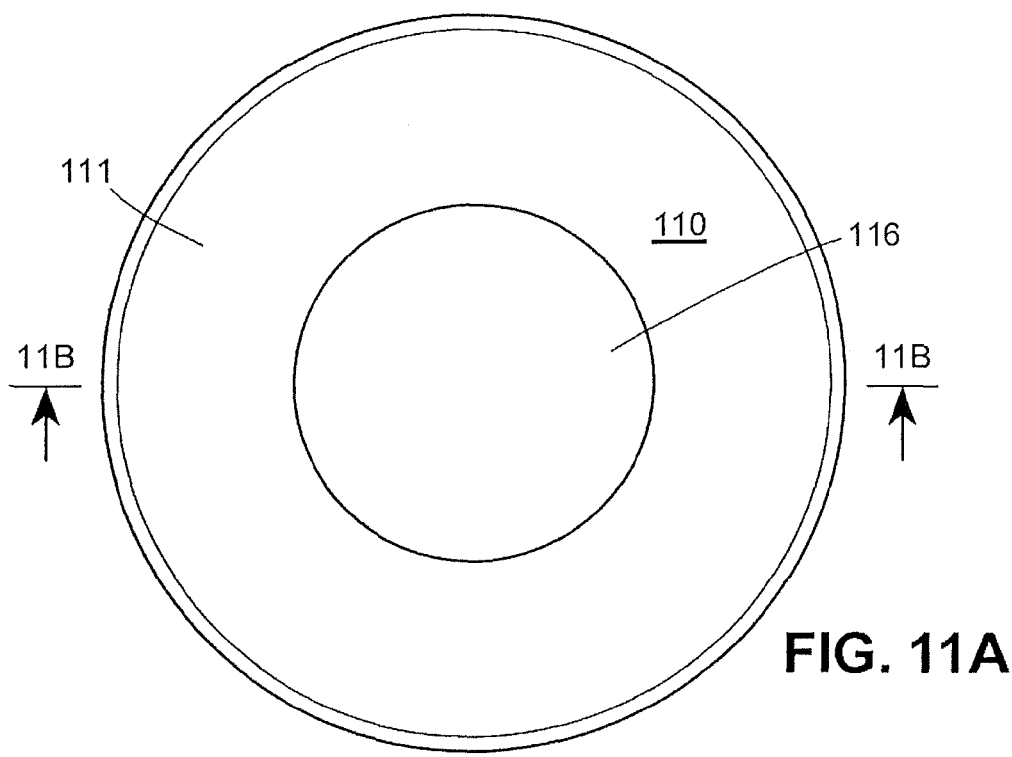
Figure 11B:
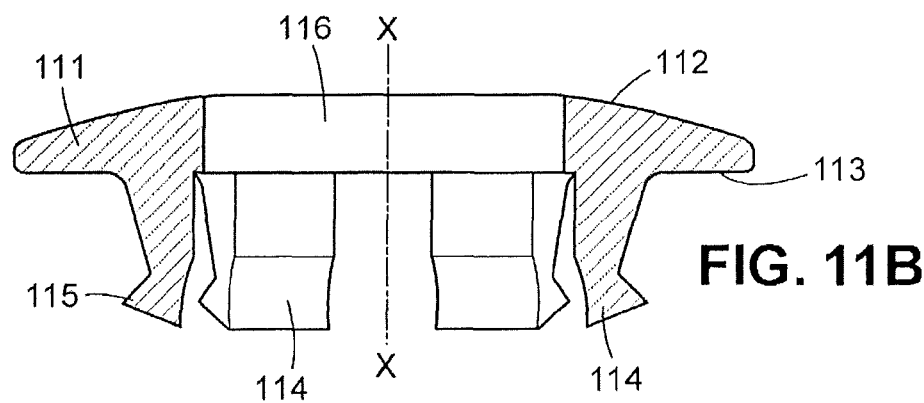

A snap-fit cranial plug 110 is illustrated in FIG. 11. The plug 110 comprises a flange 111 having an upper surface 112, a lower surface 113 and a central opening 116. Multiple legs 114 extend downwardly from the lower surface 113 and are disposed radially around central opening 116. A foot 115 extends from the distal end of each leg outwardly in a direction away from the central opening 116. The opening 116 can receive medication and/or bone growth enhancers. FIG. 11A is a top view and FIG. 11B is a section view of plug 110. Central axis x-x is illustrated in FIGS. 11A and 11B and this is typical of the central axes of the cranial plugs of the invention.

Figure 12:
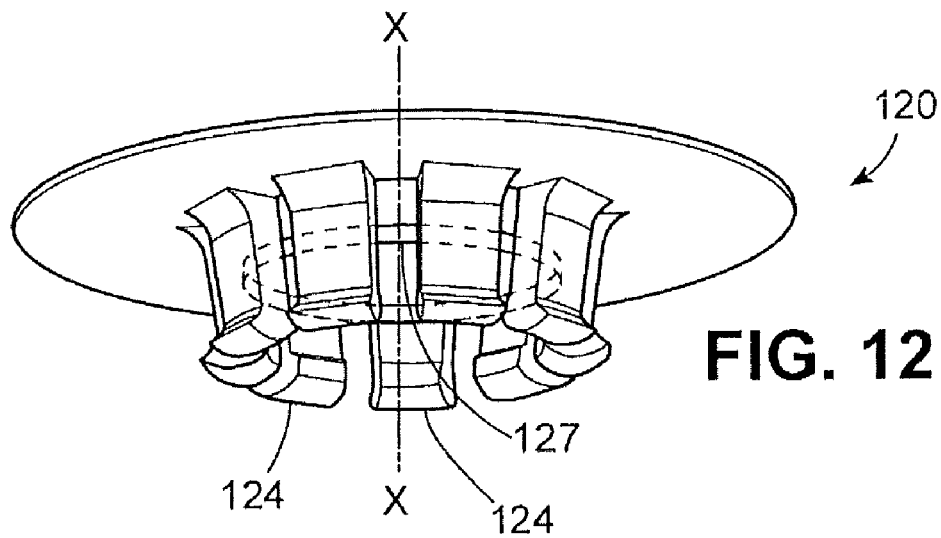
FIG. 12 is a perspective view of another cranial plug and FIGS. 12A and 12B are a top view and a section view, respectively, of the FIG. 12 embodiment.
Figure 12A:
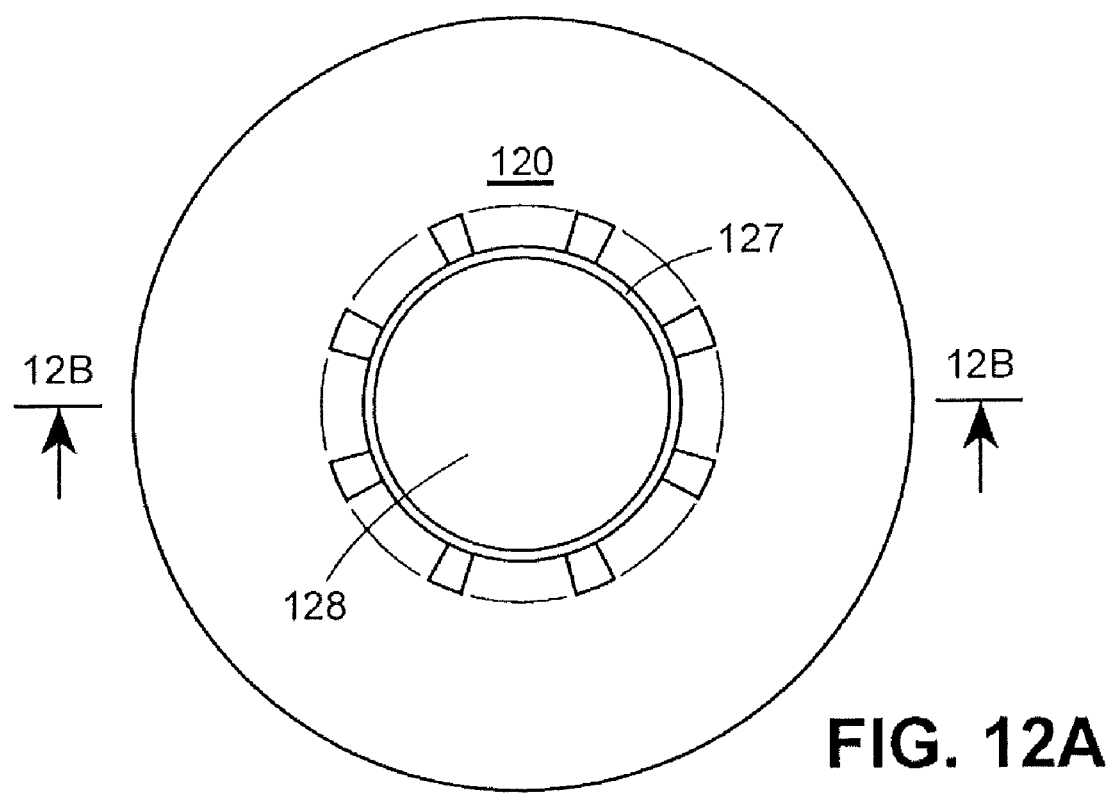
Figure 12B:
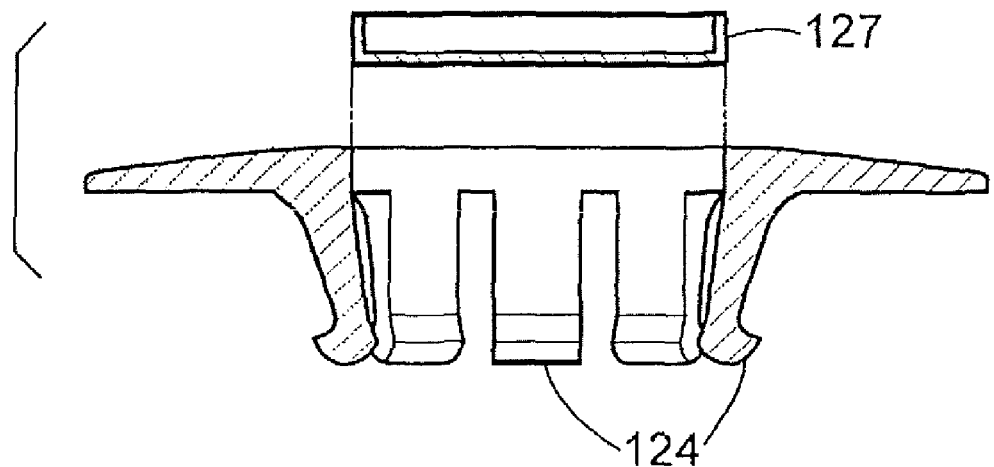
Figure 12C:
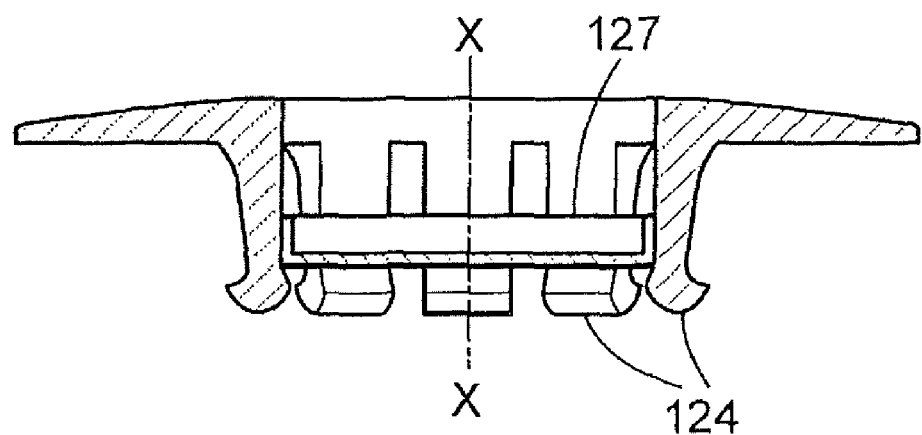

FIG. 12 illustrates in perspective another embodiment of a snap-fit cranial plug 120. A top view is provided in FIG. 12A and section views in FIGS. 12B and 12C. FIGS. 12, 12A and 12B illustrate the plug 120 in a pre-use condition and FIG. 12C illustrates the plug 120 in a use condition. Similar to the FIG. 11 embodiment, this plug has multiple legs 124 radially disposed around a central axis x-x. An axially moveable inner ring 127 is forced down toward the bottom of the legs and in doing so, expands the legs 124 away from the central axis of plug 120 and prevents the plug from dislodging when it is in use. Medication and/or bone growth enhancers and the like can be inserted through opening 128.

A cranial plug 130 is illustrated in FIG. 13 with a flange 131 and legs comprised of arcuate walls 132 having feet 133 extending outwardly therefrom. The plug 130 can be snap-fit into a burr hole or a tool can be inserted through openings 134 to compress the legs 132 inwardly when the plug is inserted into the burr hole. Then the compression is released and the legs move outwardly to secure the plug 130 in the burr hole. FIG. 13A is a top view and FIG. 13B is a section view of plug 130. The central axis is x-x.

Figure 14:
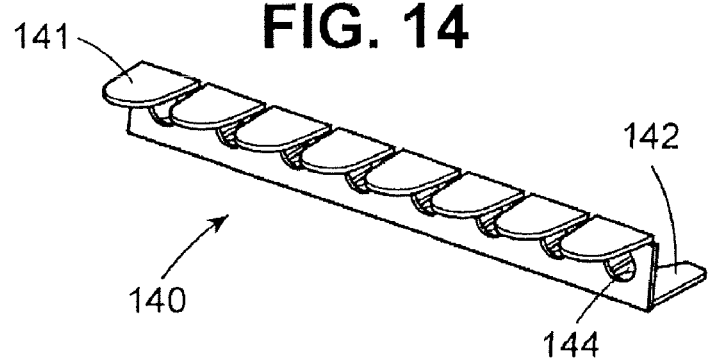
FIG. 14 is a perspective view of a cranial perforation closure and FIG. 14A illustrates the same closure after it has been bent to fill a burr hole.
Figure 14A:
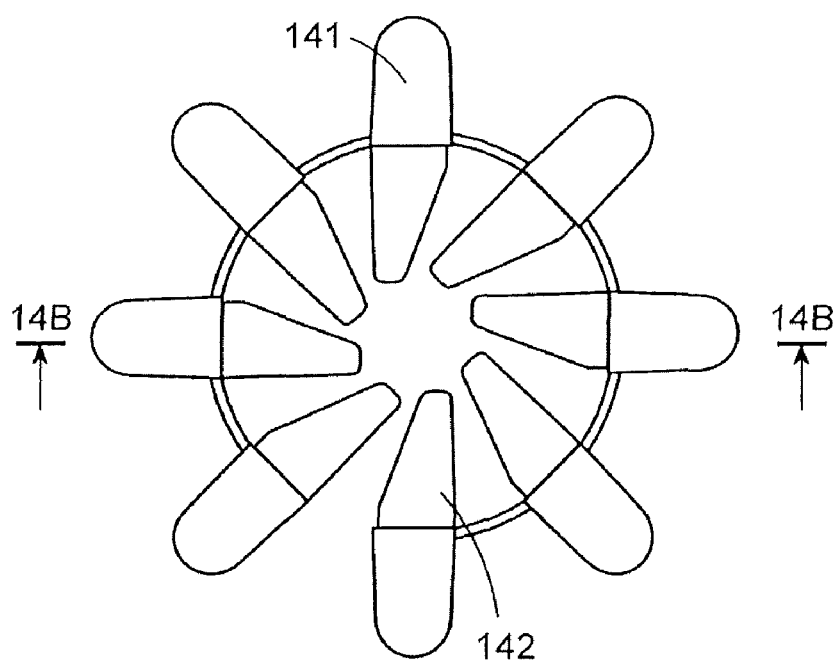
Figure 14B:
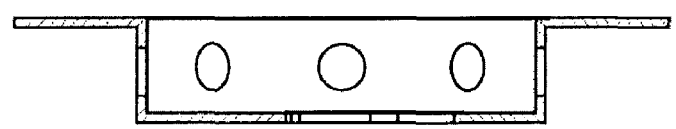
FIG. 14B is a top and section views of FIG. 14A.

FIG. 14 illustrates a cranial perforation closure 140. Shown in the straight condition, it can also be provided pre-curved and further shaped intraoperatively to conform to a burr hole as illustrated in FIG. 14A. Tabs 141 on the top surface of strip 143 attach to the skull and the skull flap. Lower tabs 142 overlap to form a floor or barrier to protect the dura and the brain. The implanted closure 140 can then be filled with bone growth enhancers or medication. Holes 144 or slots or slits (not shown) can be provided in the side walls as previously disclosed. FIGS. 14B and 14C are top and section views, respectively, of FIG. 14A.

Figure 15:
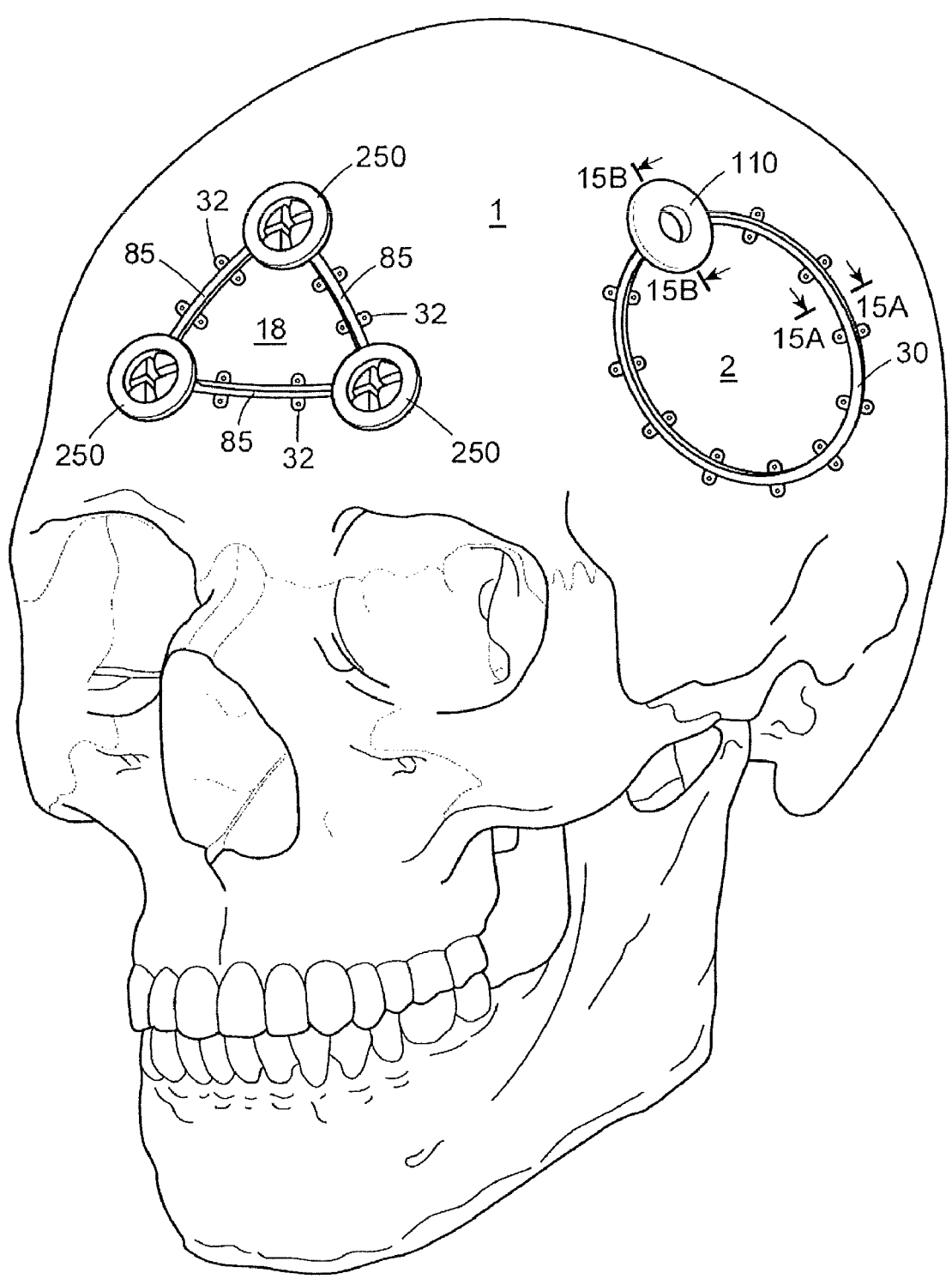
FIG. 15 is a representative view of a human skull having installed therein at one location the strip fastener of FIG. 3 and the cranial plug of FIG. 11 and at another location the strip fastener of FIG. 8B and three of the cranial plugs of FIG. 25.
Figure 15A:
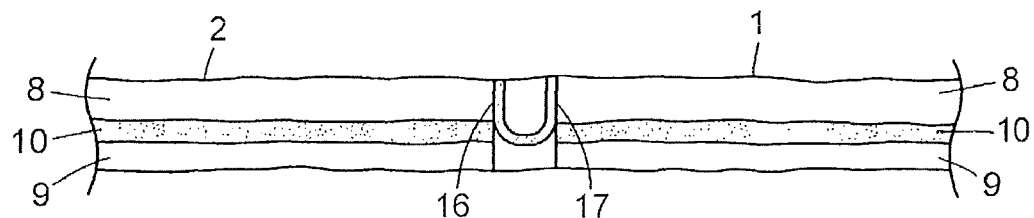
FIG. 15A is a section view taken at section line 15A of FIG. 15 illustrating the relationship of the strip fastener to the bone of the skull.
Figure 15B:
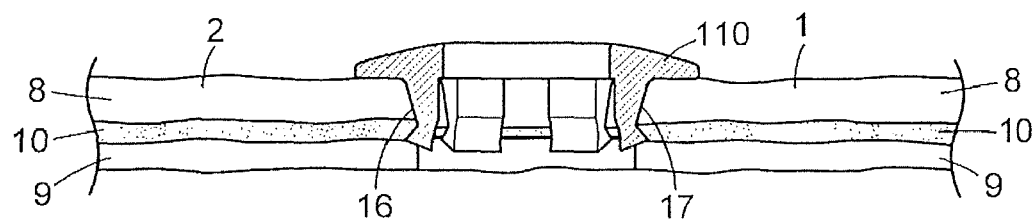
FIGS. 15B, 15C and 15D are section views taken at section line 15B of FIG. 15 showing the relationship of the cranial plug to the bone of the skull and illustrating various skull bone types and thicknesses.
Figure 15C:
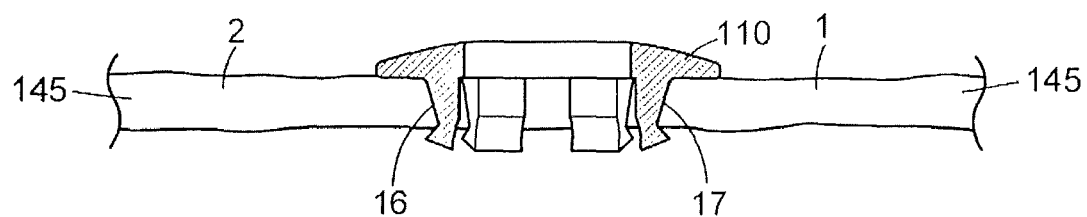
Figure 15D:
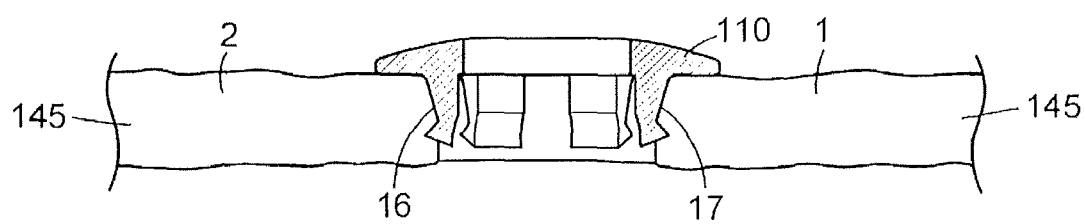

FIG. 15 illustrates a skull 1 having a skull flap 2 which has been reattached using strip fastener 30 (see FIG. 3) and cranial plug 110 (see FIG. 11) which fills a single burr hole that was used to facilitate cutting out the skull flap 2. (See FIG. 1.) FIG. 15A is a section view taken at section line 15A of FIG. 15 illustrating strip fastener 30, the skull bone 1 and skull flap bone 2. As explained above in respect of FIGS. 1A and 1B, different bone types may be encountered in the skull. FIG. 15A illustrates bone having cortical outer and inner portions 8 and 9, respectively, and a cancellous portion 10. FIGS. 15B, 15C and 15D are section views taken at section line 15B of FIG. 15 and illustrating cranial plug 110 implanted in skull 1. The side wall of the burr hole is cut when the kerf is made to cut out the skull flap 2, thus bisecting the side wall into a skull flap side wall portion 16 and a skull side wall portion 17, hereinafter referred to collectively as the side wall of the burr hole or cranial perforation. FIG. 15B illustrates the same type of cortical and cancellous bone as illustrated in FIG. 15A whereas FIG. 15C illustrates a relatively thin cortical bone 14S and FIG. 15D illustrates a relatively thick cortical bone 14T.

FIG. 15 also illustrates another skull flap 18 and this skull flap has been reattached using strip fastener 85 (see FIG. 8B) and brackets 32 (see FIG. 3) in combination with three cranial plugs 250 (see FIG. 25) which fill three burr holes that were used to facilitate cutting out the skull flap 18. It should be noted that brackets such as brackets 32 or similar brackets can be used in combination with many of the strip fasteners of the invention and most embodiments of the strip fasteners can be made without skull tabs or flap tabs if they are to be used in combination with brackets or other means to hold them in place.

Figure 16:
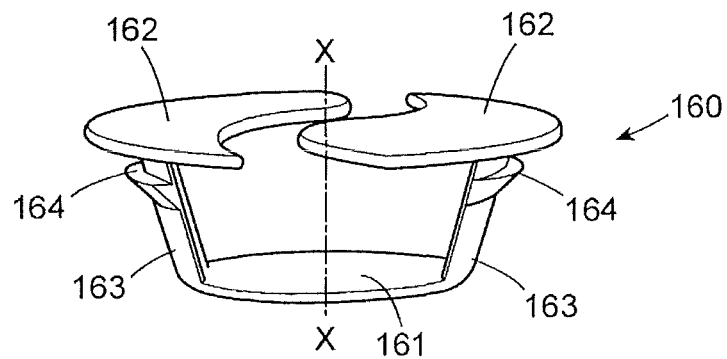
FIG. 16 is a perspective view of a cranial plug having top and side openings and FIGS. 16A, and 16B-16C are top views and section views, respectively, of the FIG. 16 embodiment.
Figure 16A:
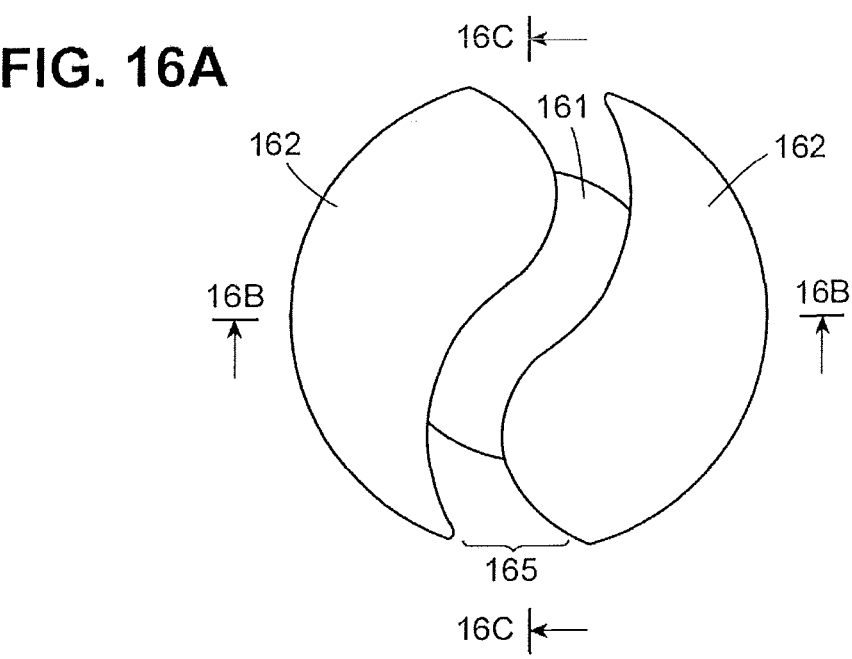
Figure 16B:
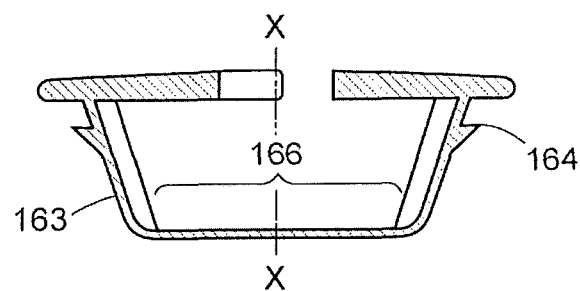
Figure 16C:
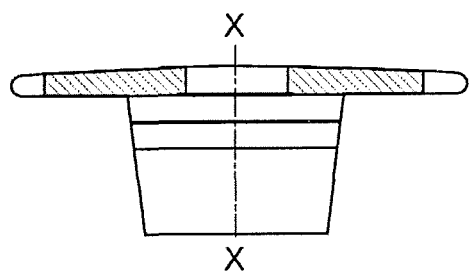

FIGS. 16, 16A and 16B illustrate a cranial plug 160 with a bottom disc shaped portion 161, a slotted top flange 162 and a central axis x-x. Tapered flexible arcuate walls 163 have one or more barbs 164 for engaging the sides of the cranial perforation (burr hole). As this plug is compressed in the burr hole, the slot 165 in the top flange 162 narrows to conform the plug to the perforation. A large opening 166 separates the side walls and passes through the entire body of the plug 160. Any of the previously described strip fasteners can be threaded through this slot so that one or more plugs can be retained by the strip fasteners when they are attached to the skull flap. Alternately the surgeon could attach brackets to the flap, insert it into the skull, insert the plug(s) into the burr holes and finally install the strip. (See FIGS. 3B-3D.) Alternatively, the strip could be threaded through the plug(s) and then the strip and plugs would be inserted into the skull. The slot 165 in the top 162 of the plug 160 allows the strip to be continuous around the perimeter of the skull flap. Holes or slots (not shown) can be provided in the side walls 163 and the slot in the top 162 allows medication and/or bone growth enhancers to be used to fill the opening 166.

Figure 17A:
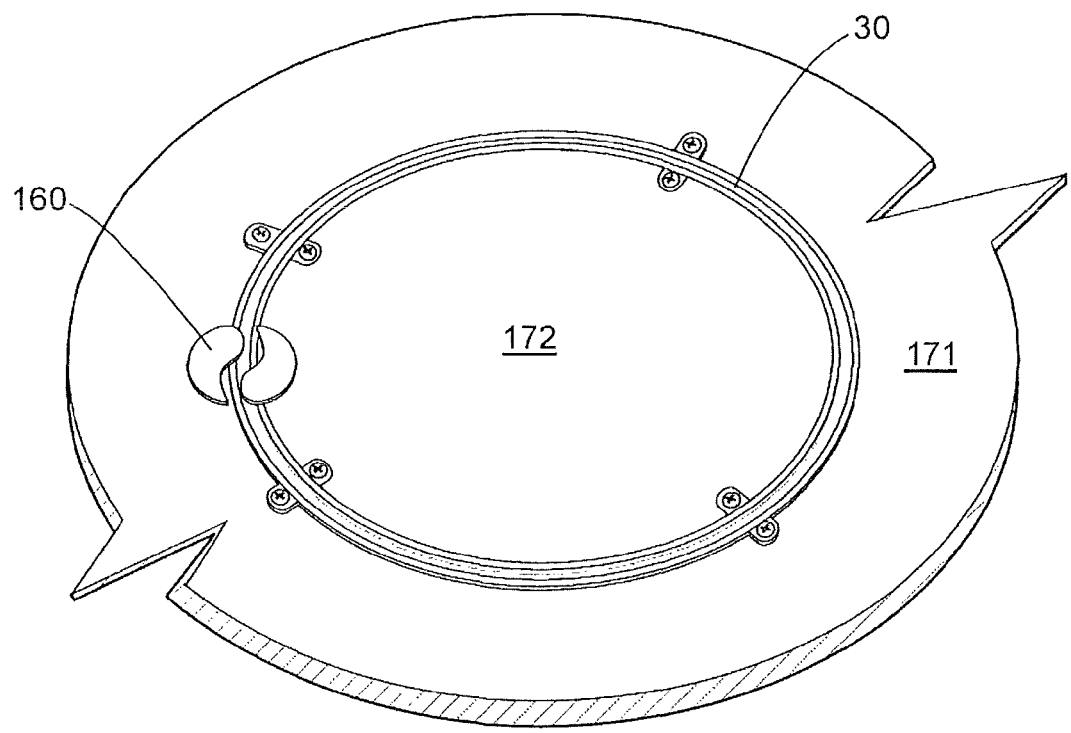
FIG. 17 is a section view of the plug of FIG. 16 and the strip fastener of FIG. 3 in a use state and FIG. 17A is a perspective view of FIG. 17.
Figure 17:
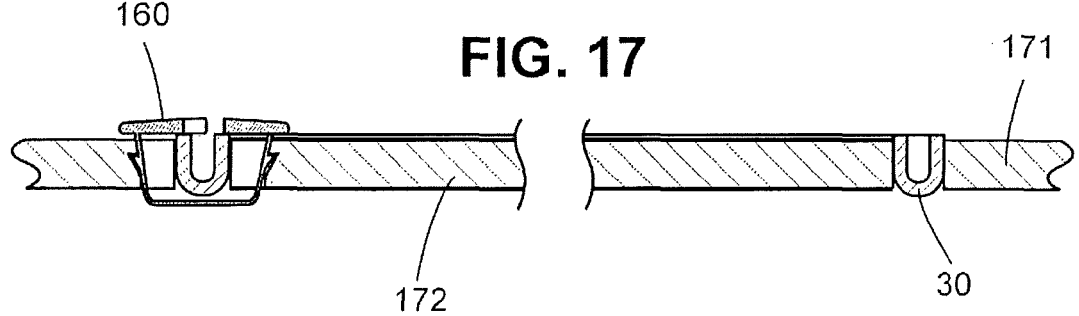

FIGS. 17 and 17A illustrate the cranial plug 160 and the strip fastener 30 (see FIG. 3) in a use state having reattached skull flap 172 to representative skull 171.

FIGS. 18, 18A and 18B illustrate cranial plug 180 with a large open area 181 between the opposing flexible arcuate walls 182. Barbs 185 are provided for engaging the sides of the burr hole. Plug 180 can be inserted into a burr hole in cases where a cranial closure strip is continuous around the perimeter of the skull flap. The large open area 181 between the side walls 182 allows the plug to straddle the strip. Holes or slots (not shown) can be provided in the side walls and opening 183 in the top 184 allows medication and/or bone growth enhancers to be used to fill the open area 181. The central axis is x-x.

FIG. 19 illustrates a strip fastener 190 with an affixed cranial plug 191 at one end of the strip 192. Surgeons who use only a single perforation for a craniotomy could use such an implant to fill the burr hole and seal the kerf. Obviously multiple combinations of the aforementioned plugs and strips can be used to make embodiments similar to FIG. 19 with one affixed plug. Additional movable plugs can be combined with such embodiments when there is a need to fill more than one burr hole.

Figure 20:
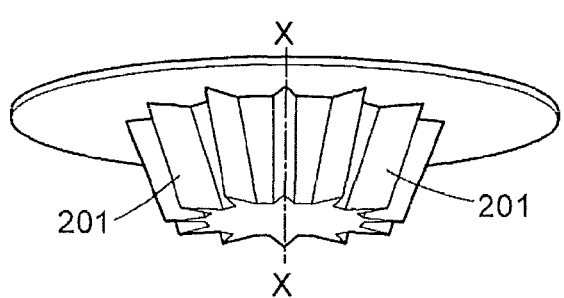
FIG. 20 is a perspective view of another cranial plug and FIGS. 20A, and 20B-20C are a top view and section views, respectively, of the FIG. 20 embodiment.
Figure 20A:
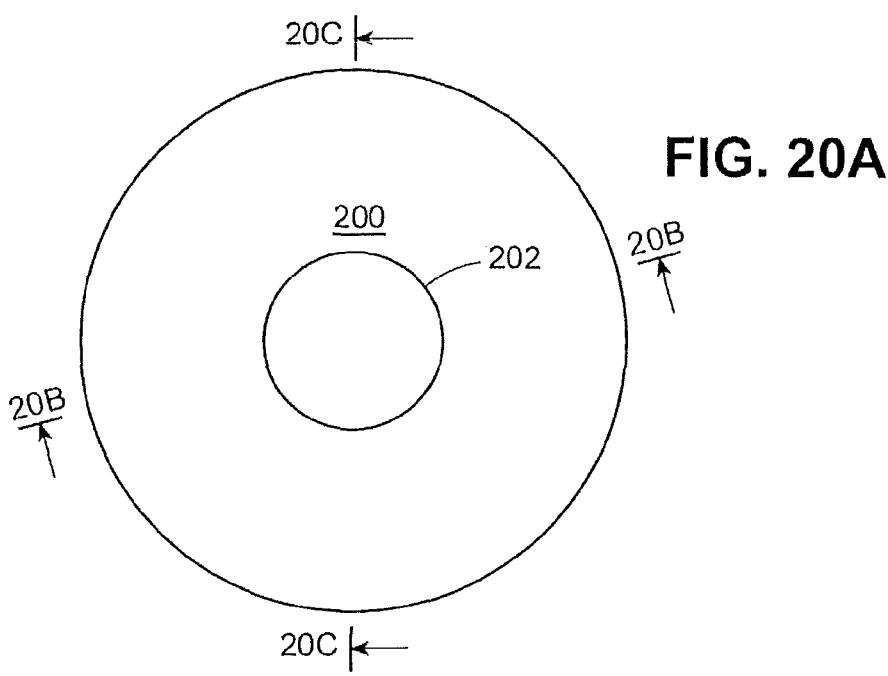
Figure 20B:
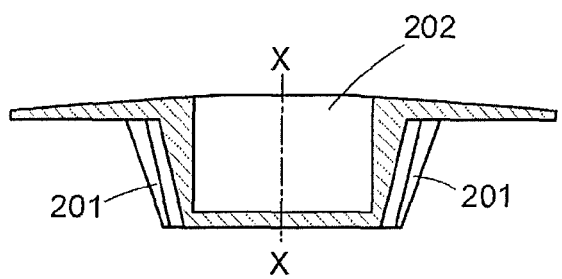
Figure 20C:
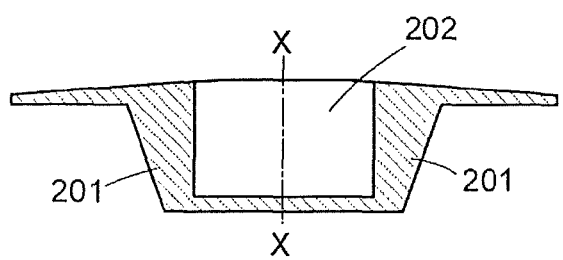

FIGS. 20, 20A and 20B illustrate a cranial plug 200 with tapered flutes 201 arranged radially about the central axis x-x. These flutes are thin and deformable such that when the plug is inserted into the burr hole, the flutes deform/conform to the walls of the perforation. The plug 200 is shown with a solid core but could also be made as a hollow part. The solid or hollow embodiments could be made with side holes, slots or slits (not shown) to encourage bone growth and/or when the plug 200 is to be filled through opening 202 with medication or bone growth enhancers or the like.

Figure 21:
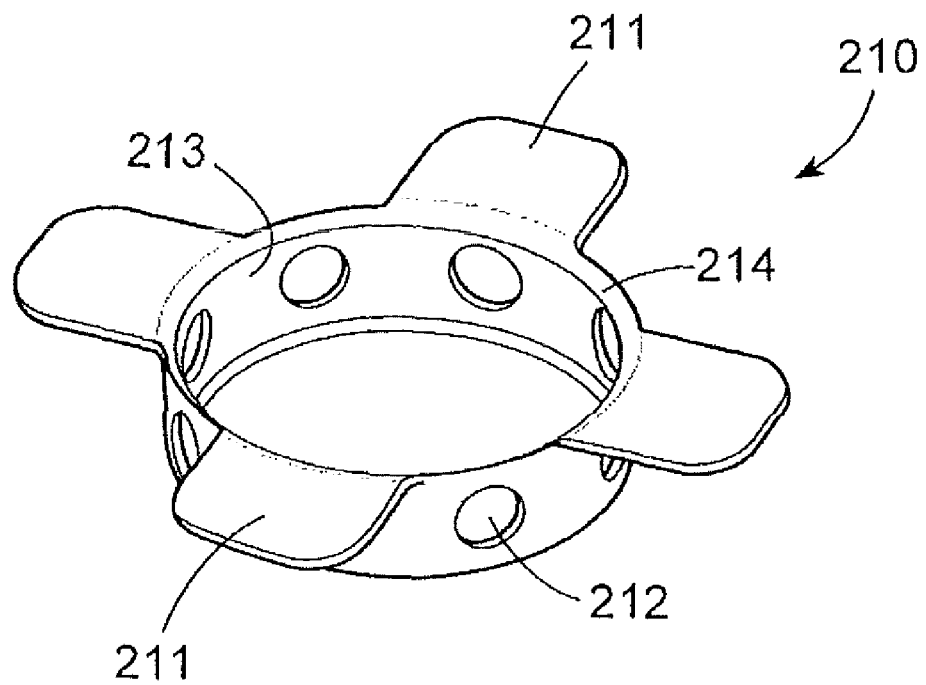
FIG. 21 is a perspective view of still another cranial plug and FIG. 21A is a section view of the FIG. 21 embodiment.
Figure 21A:
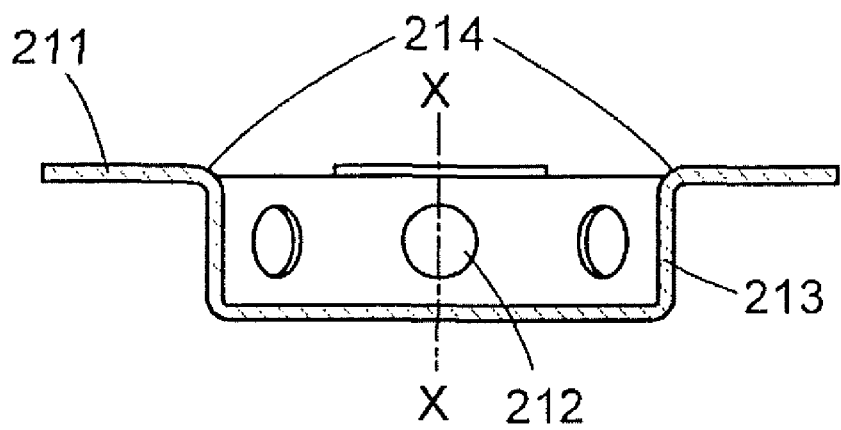

FIG. 21 illustrates a cranial plug 210 comprising a cup 213 with an upper rim 214 and external tabs 211 extending therefrom. The tabs 211 will rest upon or be affixed to the skull and flap. The cup 213 can then be filled with the appropriate additives, medications, bone growth enhancers, etc. Optional holes 212 are illustrated in the sides of the cup and these alternatively can be slots or slits (not shown).

Figure 22:
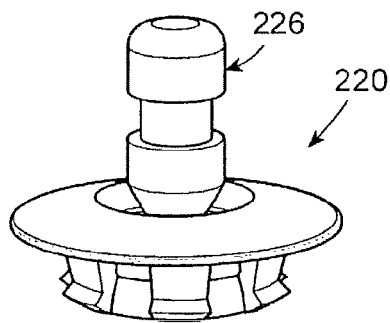
FIG. 22 is a perspective view of a cranial plug with a locking mechanism and FIGS. 22A and 22B are section views of the same.
Figure 22A:
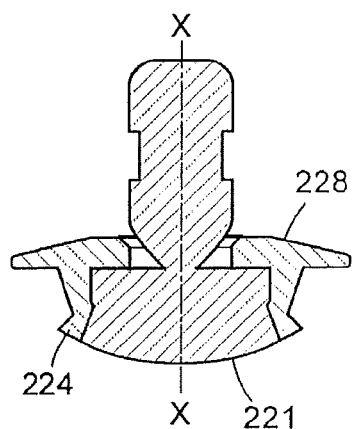
Figure 22B:
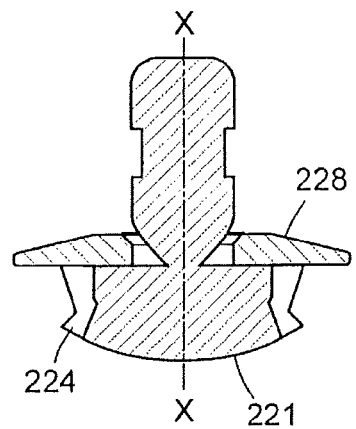
Figure 22C:
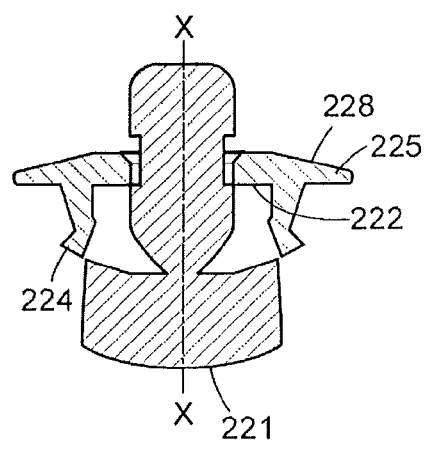
FIGS. 22C and 22D illustrates the FIG. 22 embodiment in an in-use condition.
Figure 22D:
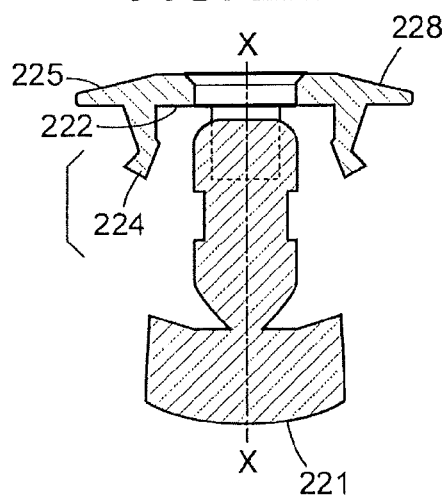

FIGS. 22 and 22A illustrate a cranial plug 220 with legs radially disposed around central axis x-x similar to that shown in FIG. 12. In this design however, the axially moveable inner element 221 is pulled upward/outward to prevent the legs 224 from deforming inward. Shown as a solid, the inner element 221 could also be hollow. Once the inner element 221 is moved to its final position adjacent the lower surface 222 of flange 225, as illustrated in FIG. 22A, the removable stem 226 can be snapped off below the level of the top 228 of the plug. View 22B illustrates the in-use condition of plug 220.

Figure 23:
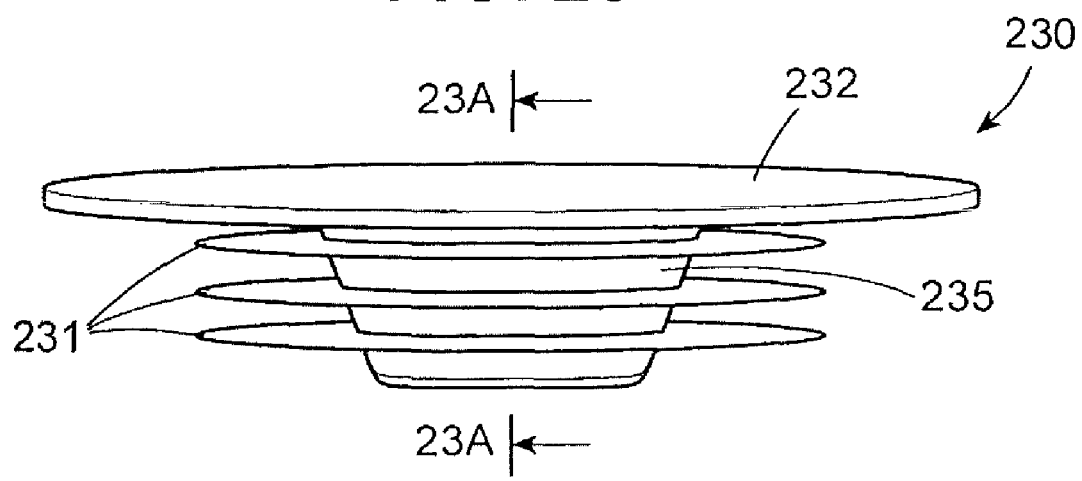
FIG. 23 is a perspective view of a cranial plug and FIG. 23A is a section view of the FIG. 23 embodiment.
Figure 23A:
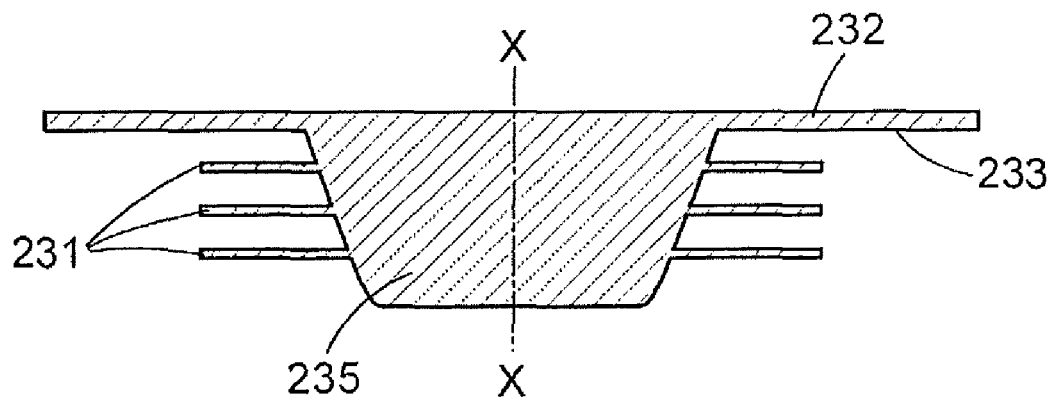

FIGS. 23 and 23A illustrate a cranial plug 230 having a central axis x-x, a frustoconical extension 235 with thin flutes 231 in the form of flexible circular vanes disposed thereon and oriented in planes parallel to the lower surface 233 of flange 232. Similar to the plug shown in FIG. 20, these thin flutes would deform/conform when inserted into the burr hole. Shown as a solid, it too could be provided with a hollow core and cross holes/slots.

Figure 24:
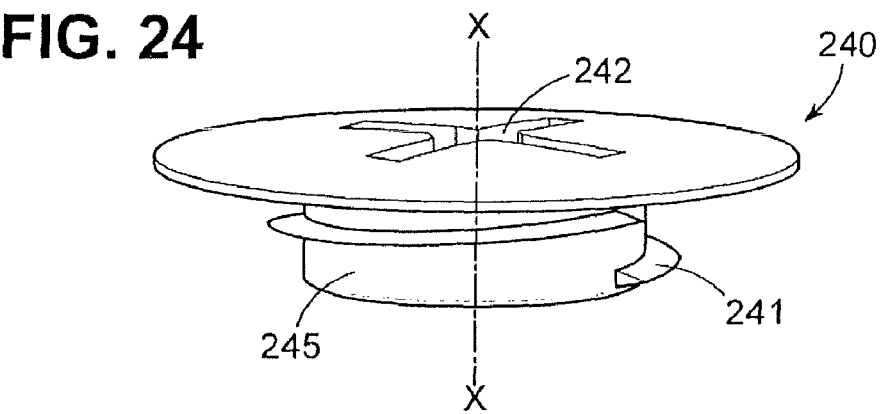
FIG. 24 is a perspective view of a cranial plug.
Figure 24A:
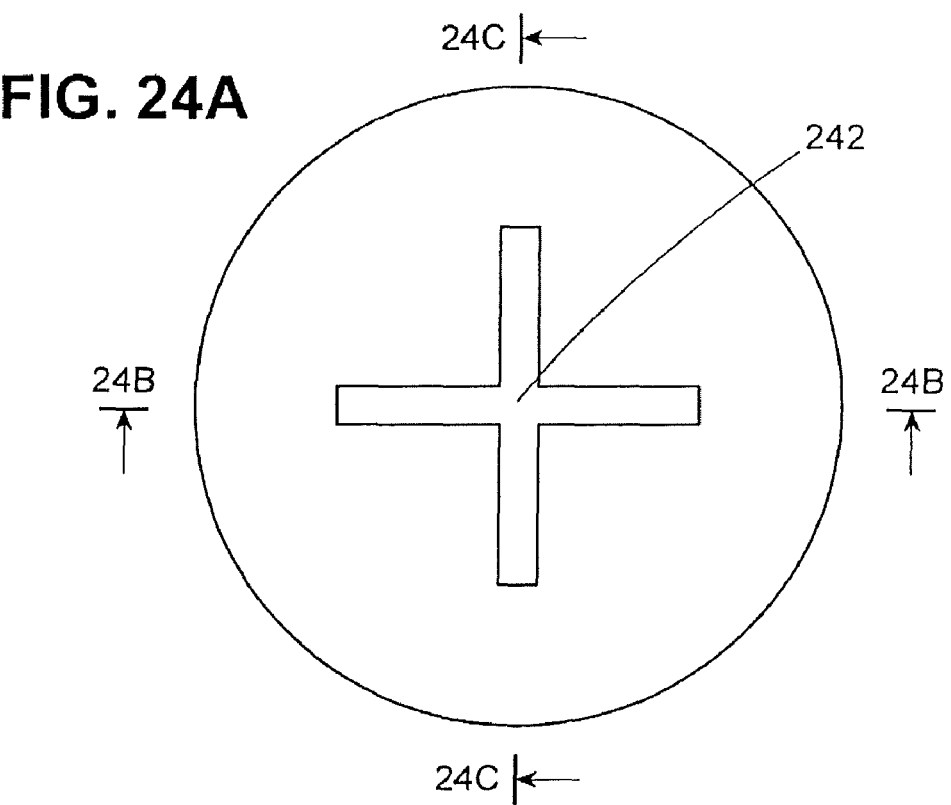
FIG. 24A is a top view and FIG. 24B is a section view of the FIG. 24 embodiment.
Figure 24B:
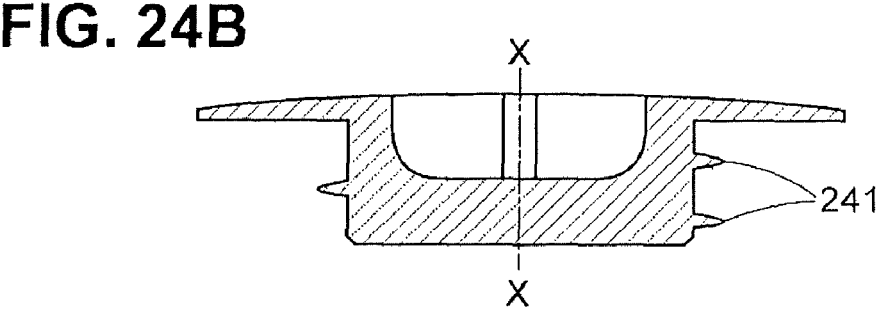
Figure 24C:
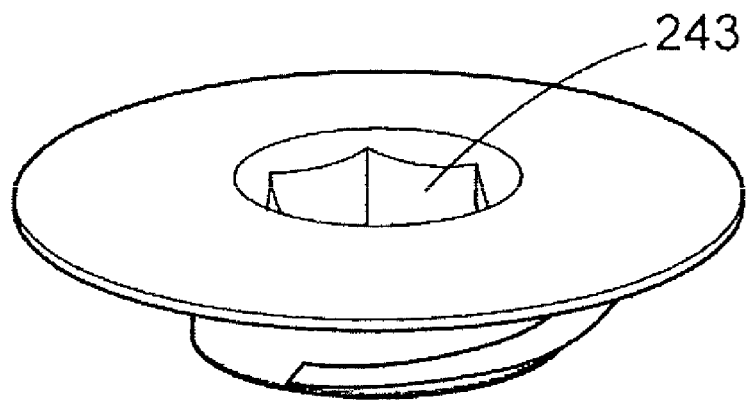
FIGS. 24C and 24D are perspective views of alternatives to the FIG. 24 embodiment.
Figure 24D:
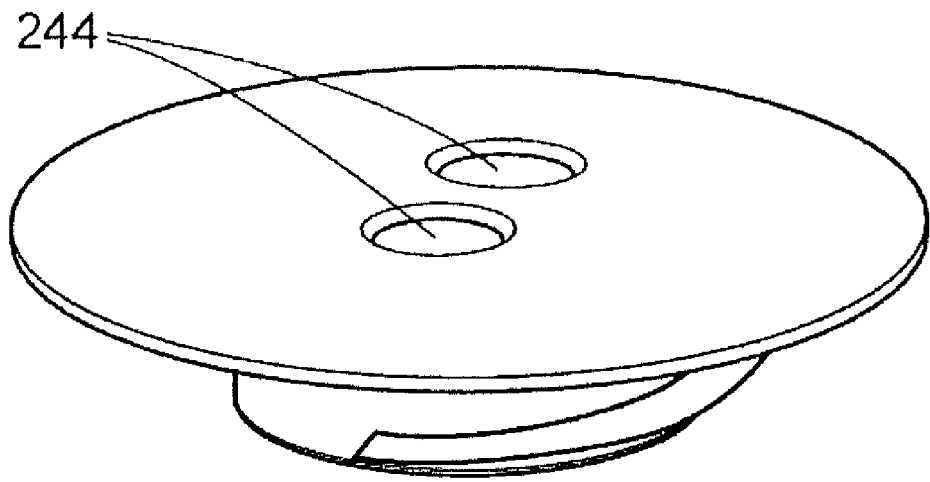

FIGS. 24, 24A, 24B, 24C and 24D illustrate a cranial plug 240 having a central axis x-x, a cylindrical extension 245 and disposed thereon a tapered helical thread 241 having a thin cross-section. It is designed to be rotated/screwed into the burr hole and it is expected that the thread will deform/conform to the bony side walls. Different drive mechanisms are shown. FIGS. 24, 24A and 24B illustrate a cruciform drive opening 242. FIG. 24C shows a hex drive opening 243 and FIG. 24D shows a spanner drive opening 244. Shown as solid plugs, they could also be produced in hollow forms with cross holes, slots and/or slits (not shown).

Figure 25:
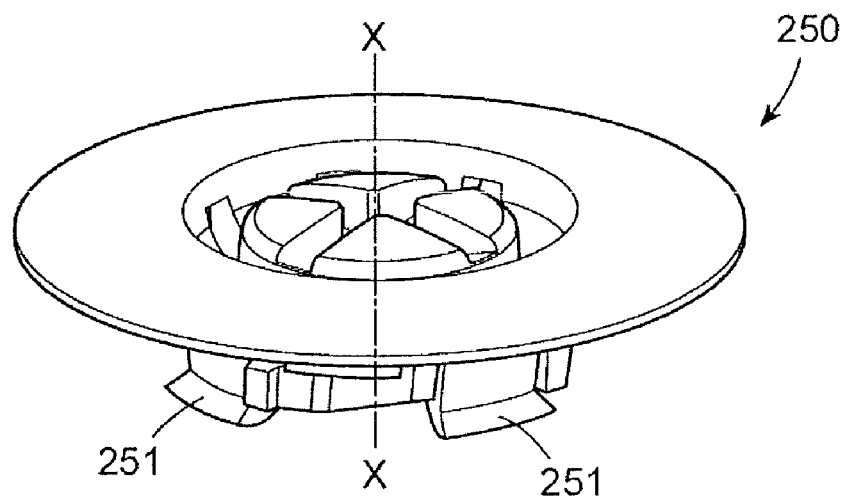
FIG. 25 is a top perspective view of a cranial plug having a cam lock.
Figure 25A:
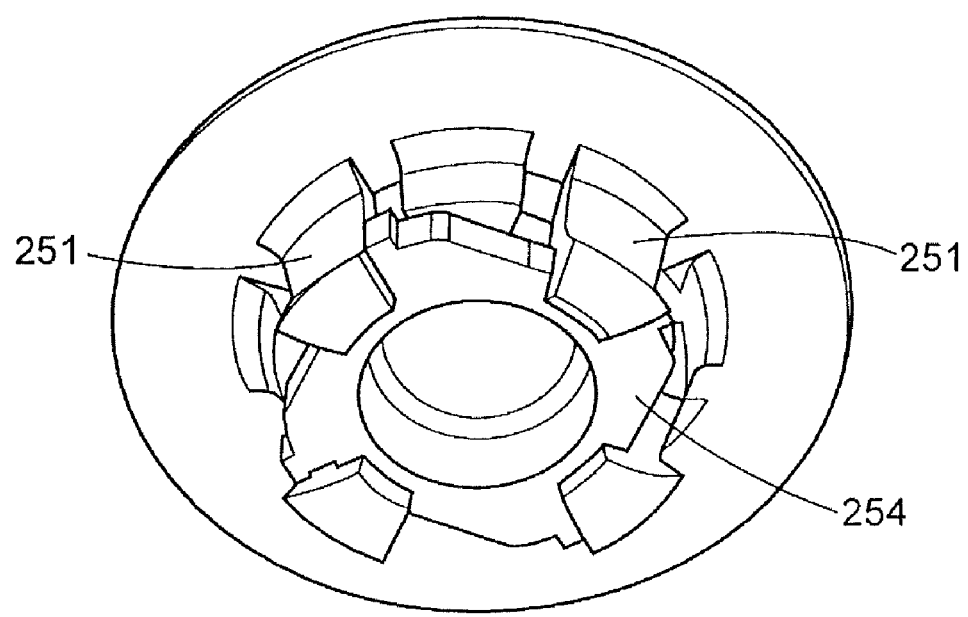
FIG. 25A is a bottom perspective view of the FIG. 25 embodiment and FIG. 25B is a top view.
Figure 25B:
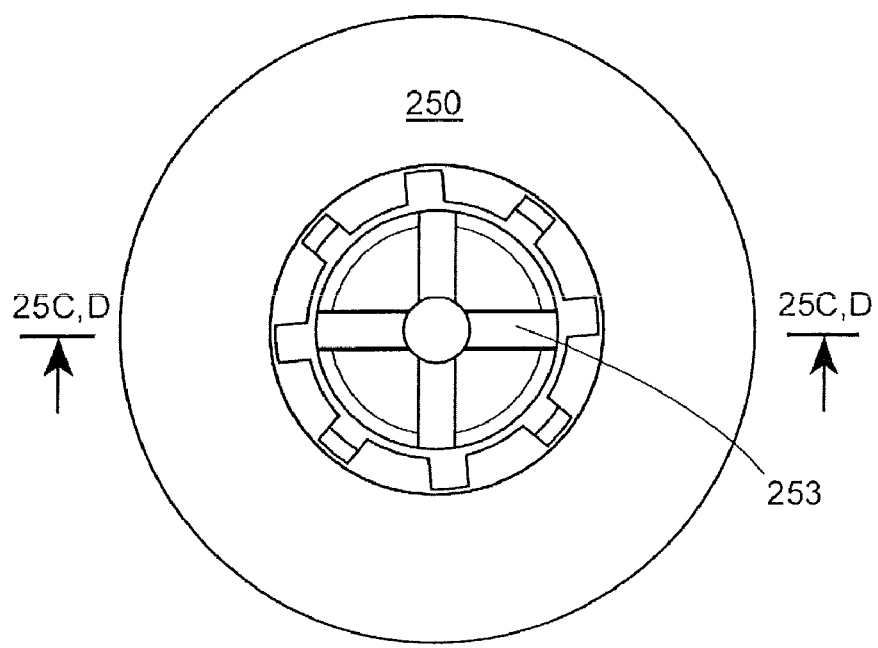

FIGS. 25, 25A and 25B illustrate a cranial plug 250 with radially disposed legs 251 similar to those shown in FIG. 12 and FIG. 20. FIG. 25 is a top perspective view, FIG. 25A is a bottom perspective view and FIG. 25B is a top view. In this case, a moveable inner cam 254 rotates around the central axis x-x so that it contacts the legs 251 to push them outward, holding them in the outward position and preventing them from deflecting inward. A cruciform drive recess 253 is shown but other drive mechanisms are possible. The figures illustrate plug 250 with cam 254 in the pre-use position wherein the legs 251 have not yet been pushed outwardly.

Figure 25C:
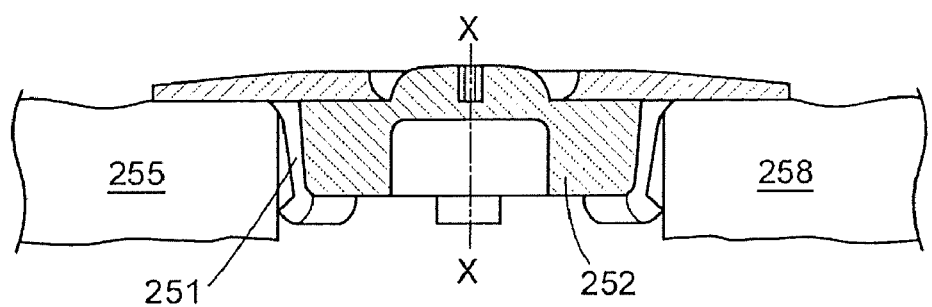
FIGS. 25C and 25D are section views of the FIG. 25 embodiment installed in a skull.
Figure 25D:
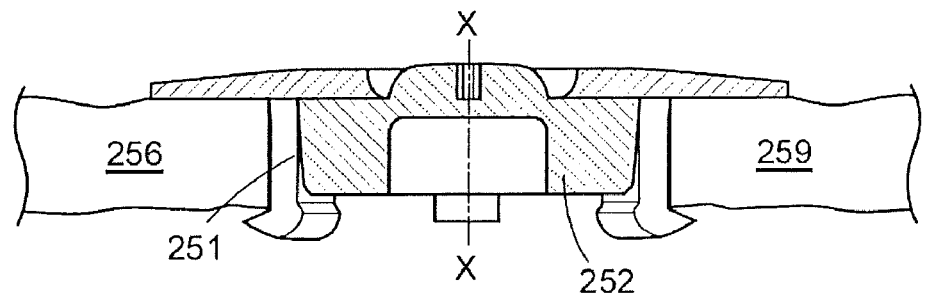

FIGS. 25C and 25D illustrate in section views the cranial plug 250 in a use condition. In FIG. 25C the skull flap 255 and skull 258 are relatively thick and in FIG. 25D the skull flap 256 and skull 259 are relatively thin.

Figure 26:
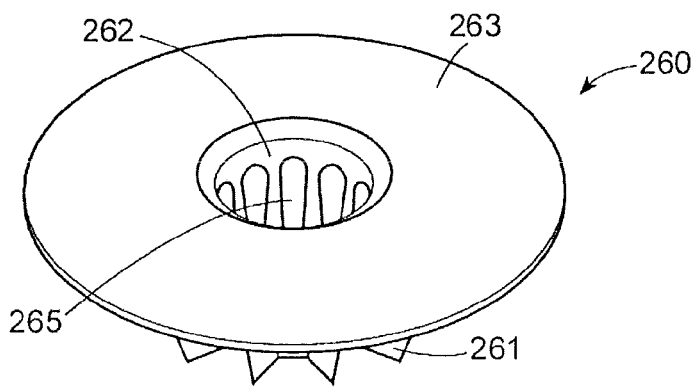
FIG. 26 is a perspective view of a cranial plug having flexible vanes.
Figure 26A:
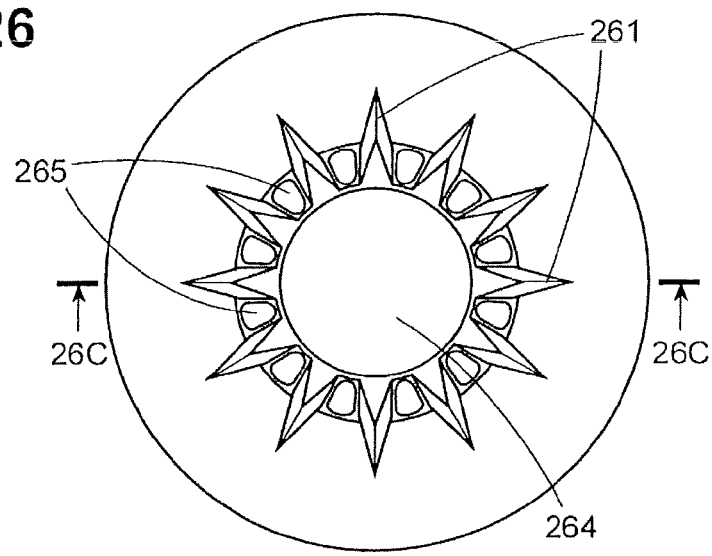
FIG. 26A is a bottom view.
Figure 26B:
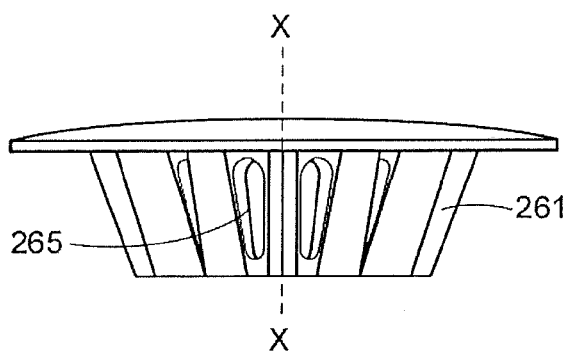
FIG. 26B is an elevation view and FIG. 26C is a section view of the FIG. 26 embodiment.
Figure 26C:
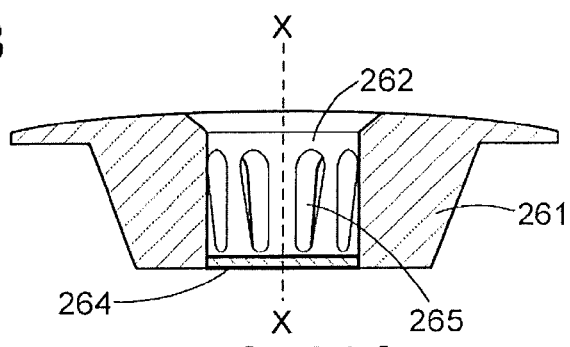

FIG. 26 is a perspective view of cranial plug 260. FIG. 26A is a bottom view, FIG. 26B is an elevation view and FIG. 26C is a section view. The plug 260 has a central axis x-x and flexible vanes 261 which press fit against the sides of a burr hole when plug 260 is in use. Optional opening 262 in top 263 of plug 260 allows for medication to be inserted and optional floor disc 264 holds the medication in place. Optional openings 265 serve the same function as the holes, slits or slots in other embodiments of the plugs and strip fasteners of the invention.

Figure 27:
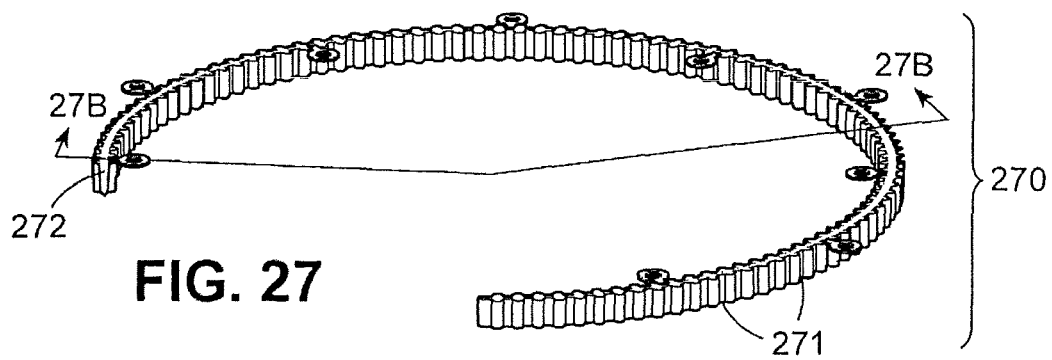
FIG. 27 is a perspective view of a strip fastener having lateral corrugations and FIG. 27A is a section view thereof.
Figure 27A:
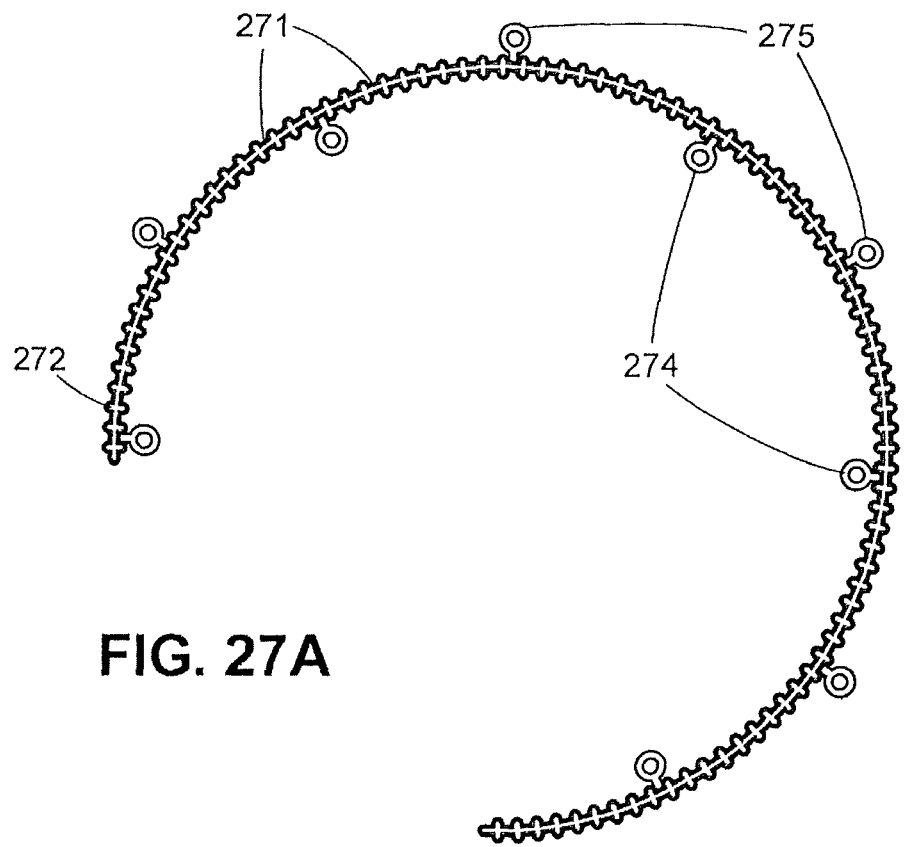
Figure 27B:
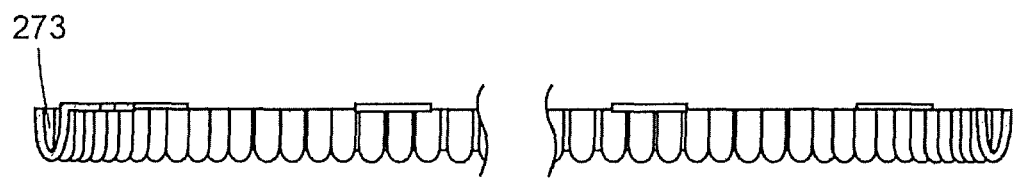
FIG. 27B is a section view of the FIG. 27 embodiment.

FIG. 27 illustrates strip fastener 270 having lateral corrugations 271 which facilitate bending without kinking. A top view is illustrated in FIG. 27A and a section view is illustrated in FIG. 27B. In a use state, the opening 272 is arranged so that medication and the like can easily be added to fill the cavity 273. The fastener 270 has flap tabs 274 and skull tabs 275 for affixing the fastener to the skull flap and skull. Holes, slots or slits can be provided as with many of the other strip fastener embodiments of the invention.

Figure 28:
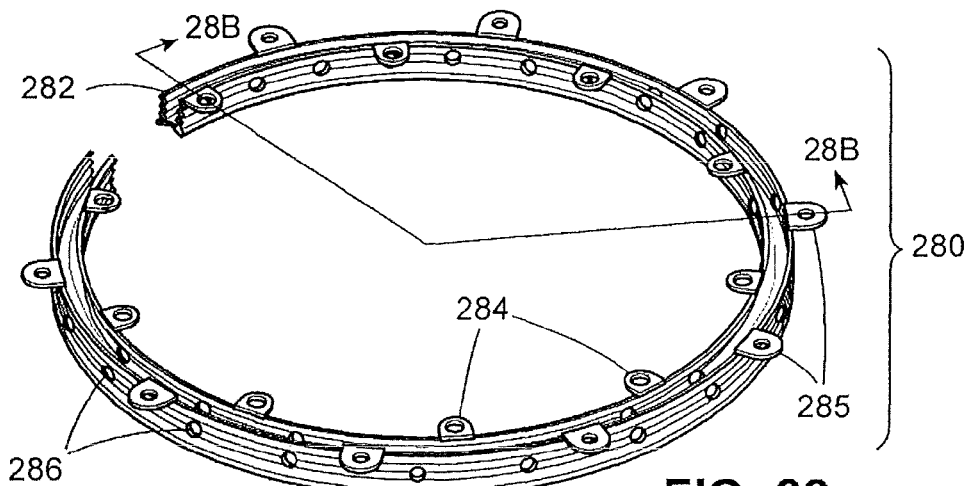
FIG. 28 is a perspective view of a strip fastener having longitudinal corrugations.
Figure 28A:
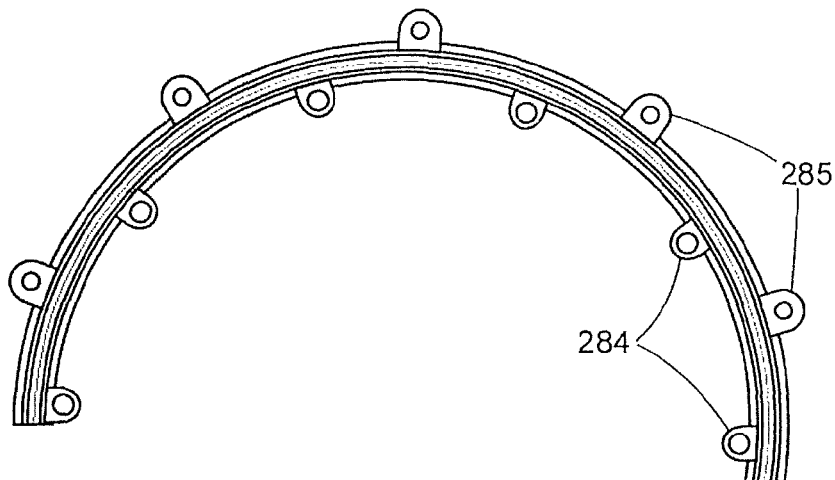
FIG. 28A is a top view of the FIG. 28 embodiment and FIG. 28B is a section view thereof.
Figure 28B:
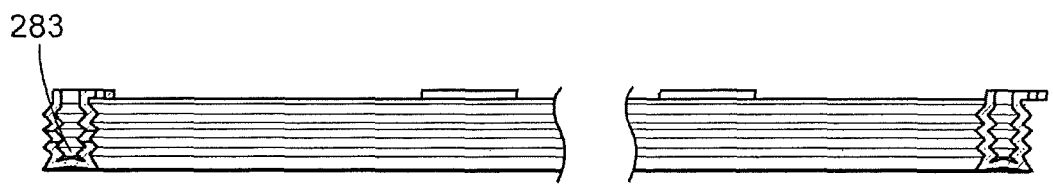

FIG. 28 illustrates strip fastener 280 having longitudinal corrugations 281 which facilitate bending and provide added surface area. A section view is illustrated in FIG. 28A. In a use state, the opening 282 is arranged so that medication and the like can easily be added to fill the cavity 283. The fastener has flap tabs 284 and skull tabs 285 for affixing the fastener to the skull flap and skull. Holes 286 are illustrated but slots or slits can be provided alternatively or in addition to the holes as with many of the other strip fasteners of the invention.

Figure 29:
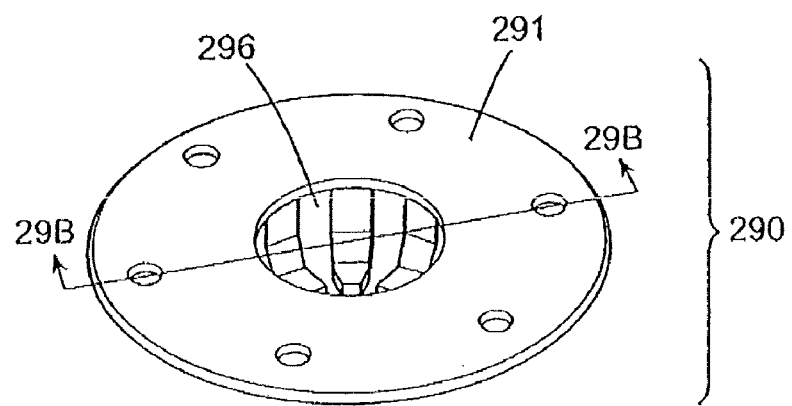
FIG. 29 is a perspective view of a cranial plug having flexible ribs.
Figure 29A:
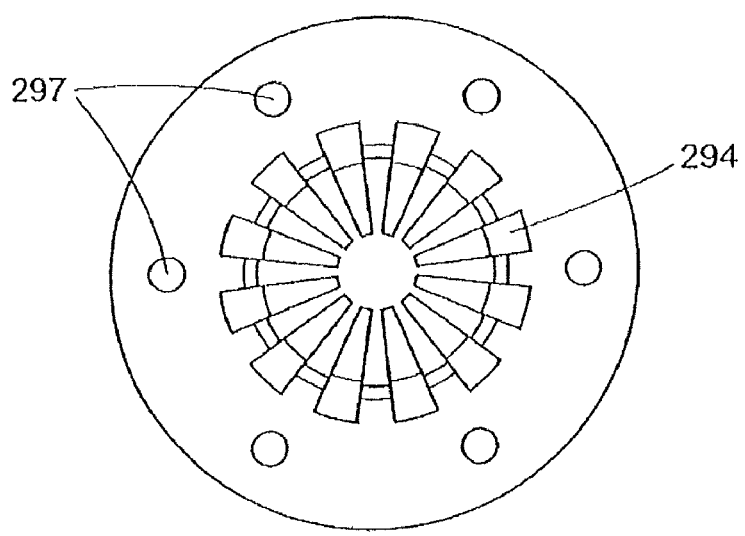
FIGS. 29A and 29B are a bottom view and a section view, respectively.
Figure 29B:
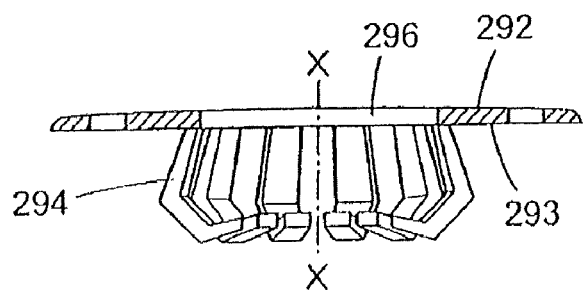

A snap-fit cranial plug 290 is illustrated in FIGS. 29, 29A and 29B. The plug 290 comprises a flange 291 having an upper surface 292, a lower surface 293 and a central opening 296 concentric with central axis x-x. Multiple flexible ribs 294 extend downwardly from the lower surface 293 and are disposed radially around central opening 296. The ribs 294 are shaped to facilitate a snap-fit when the plug 290 is pushed into a burr hole. The proximal ends of the ribs 294 are affixed to the lower surface 293 of the flange 291. As the ribs extend downwardly they taper away from the central axis toward an elbow. At the elbow, the direction of the taper is turned inwardly toward the central axis and continues to the distal ends of the ribs. Optionally, as shown in FIG. 29, a second elbow is provided at the distal ends whereupon the ribs are tapered toward the central opening 296 as the ribs approach the central axis. Optional holes 297 are provided for fasteners such as screws. Screws may be used, for example, when the plug 290 is to be fastened at the burr hole portions of a skull flap. Then the skull flap can be snap-fit into the skull without the need for additional fasteners. This is especially advantageous in surgeries wherein the skull flap may need to be removed at a later date for additional surgery or diagnostic procedures.

Figure 29C:
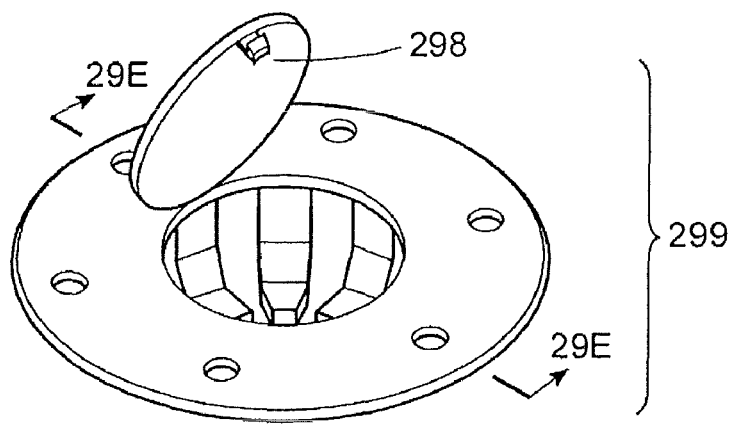
FIG. 29C is a perspective view of an alternate embodiment of the FIG. 29 plug and FIGS. 29D and 29E are a top view and a section view, respectively, of the alternate embodiment.
Figure 29D:
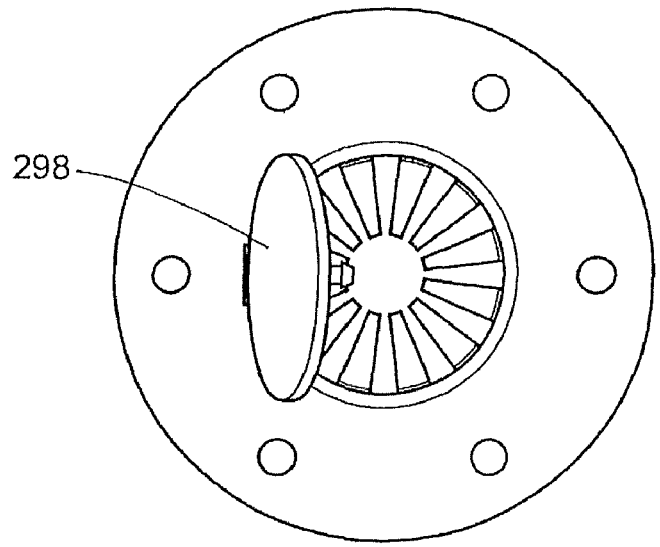
Figure 29E:
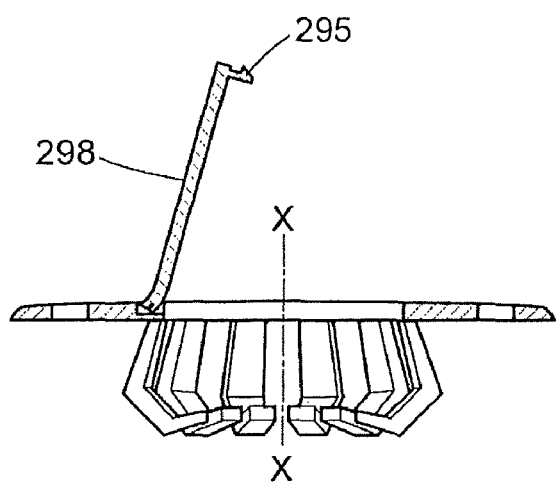

FIGS. 29C, D and E illustrate snap-fit cranial plug 299 which is an alternative embodiment of the FIG. 29 plug having a hinged lid 298 thereon. Latch 295 on hinged lid 298 allows the lid to be snapped closed in order, for example, to prevent medication from coming out of the central opening of the plug or to prevent soft tissue from prolapsing into the cavity. Obviously the cap could be entirely removable (no hinge) and secured by many of the same methods disclosed herein to retain a plug in a burr hole.

Figure 29F:
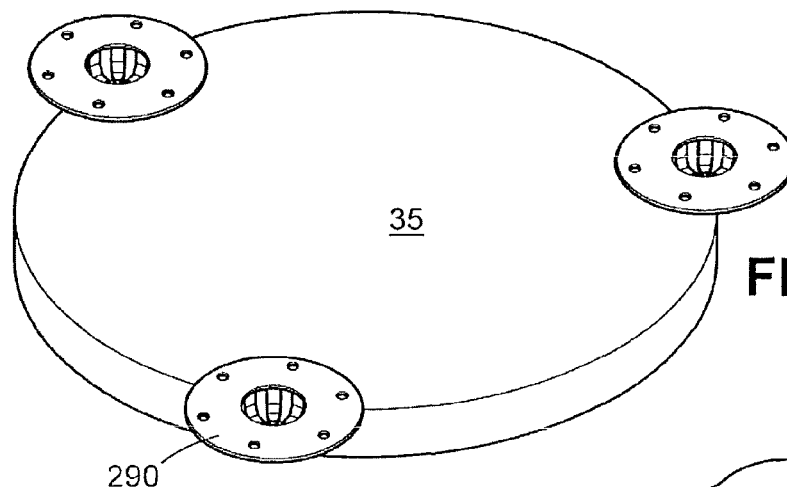
FIG. 29F illustrates the FIG. 29 plug in perspective in relationship to a skull flap and FIGS. 29G and 29H illustrate the FIG. 29 plug installed in a skull.
Figure 29G:
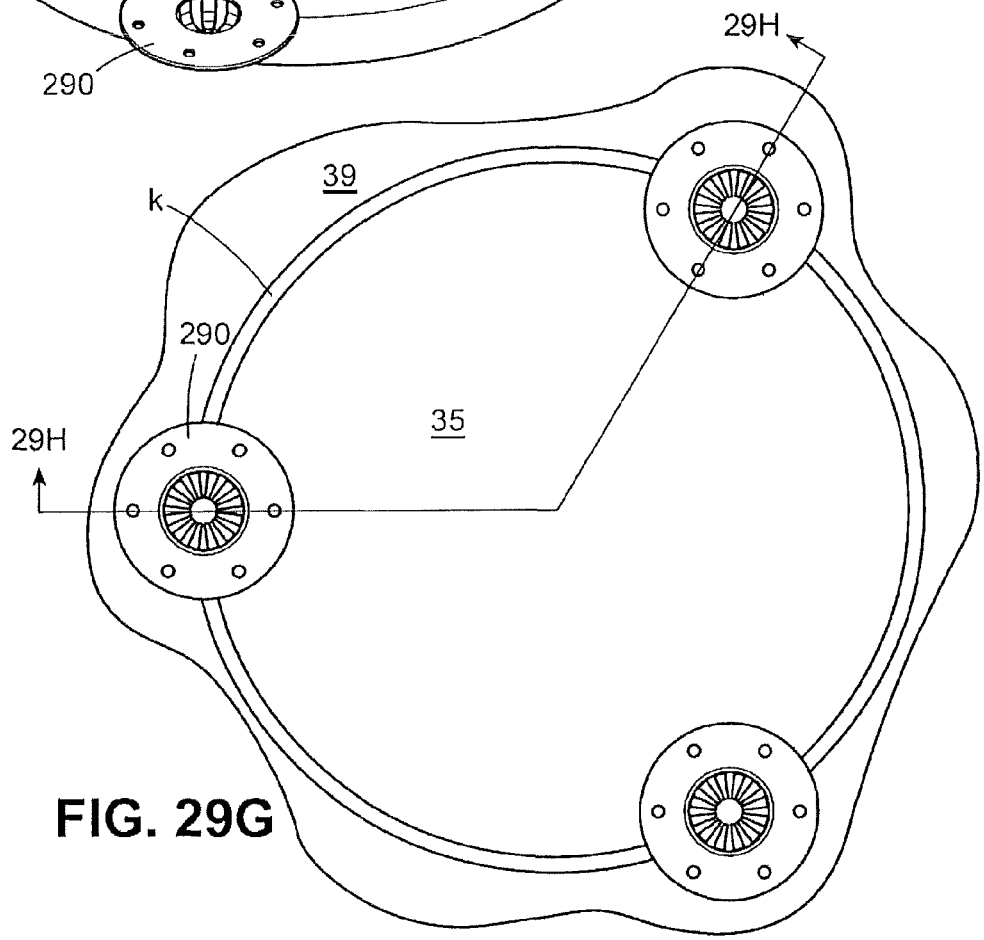
Figure 29H:
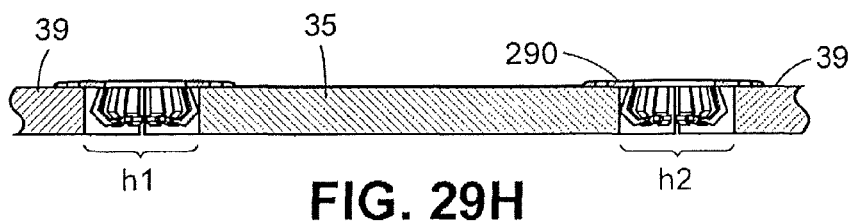

FIG. 29F illustrates in perspective a skull flap 35 wherein three plugs 290 have been adhered at three burr hole portions disposed around the perimeter of flap 35. FIGS. 29G and 29H are top and section views, respectively, of the skull flap 35 installed in the skull 39 using the plugs 290. Section view FIG. 29H illustrates two of the burr holes, h1 and h2. Kerf k can optionally be filled with one of the strip fasteners of the invention.

The strip fastener 300 illustrated in FIGS. 30, 30A and 30B is comprised of a J-shaped flexible strip 301 which is pre-curved and sufficiently flexible to be shaped to follow the perimeter contour of a skull flap. As with the other strip fastener embodiments of the invention, the strip fastener 300 can have integral tabs on the inside perimeter 307 or both the inside perimeter 307 and the outside perimeter 308. This embodiment has been illustrated with an elongate flange 302 which spans the cavity and forms a continuous tab on both the inside and outside perimeters. A vertical rib 304 connects the cavity to the flange 302. In this embodiment, the vertical rib 304 purposely positions the J-shaped cavity below the level of the underside of the flange 303 to insure that the J-shaped flexible strip 301 remains below the top surface of the skull and skull flap.

Figure 31:
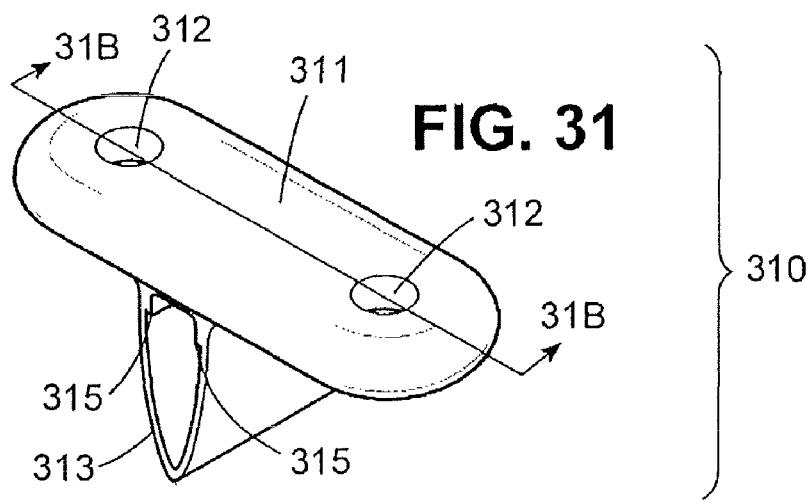
FIG. 31 is a perspective view of a fastener of the invention which is used in conjunction with strip fasteners, for example, as illustrated in FIG. 30.
Figure 31A:
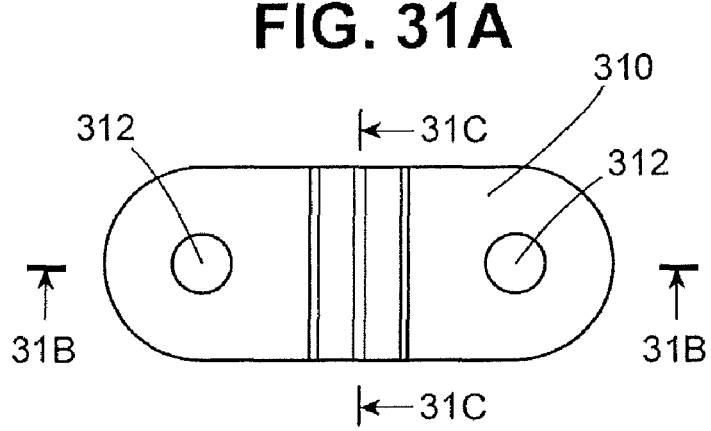
FIG. 31A is a bottom view and FIGS. 31B and C are section views of the FIG. 31 fastener.
Figure 31B:
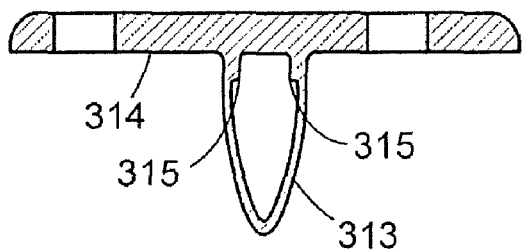
Figure 31C:
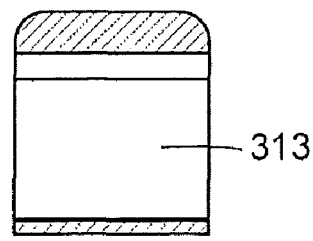

FIG. 31 illustrates a perspective view of a V-shaped bracket 310 with a continuous elongate flange 311 creating tabs 318 on both sides of the kerf. Optional fastener holes 312 are shown in each tab 318. A V-shaped projection 313 having an aperture 316 projects from the underside of the flange 314 and is meant to fit around a compatibly shaped flexible strip 317 (without tabs). In other words, the strip 317 is threaded through the aperture 316 in the V-shaped projection 313 of bracket 310. Optional tabs 315 on the inside of the aperture 316 position the strip 317 at a distance below the underside of the flange 314. These brackets could be affixed to the strip or could be able to slide along its length. Obviously other strip cross sections (U, J, W, tubular) could be used in a similar manner.

What is claimed is:

1. A strip fastener for reattaching a skull flap removed from a skull during brain surgery, the skull flap having a top surface, a bottom surface and a perimeter defined by a bone edge surface, the bone edge surface having a vertical component extending from the top surface to the bottom surface and a horizontal component extending around the perimeter in a lateral direction, the strip fastener comprising a flexible strip having a bottom portion and a top portion and having length and sufficient flexibility to be formed lengthwise around the perimeter in the lateral direction and alongside the bone edge surface, the strip having a plurality of flap tabs spaced along the length of the bottom portion of the strip and in engagement thereto, and a plurality of skull tabs spaced along the length of the top portion of the strip and in engagement thereto, wherein the flap tabs protrude transversely to the length and away from the bottom portion of the strip and protrude perpendicularly to the skull tabs;

wherein the flap tabs are adapted to be disposed over and adjacent to the skull flap and the skull tabs are adapted to be disposed over and adjacent to the skull when the strip is positioned alongside the bone edge surface, and wherein the flap tabs are structured to be attached to the to the skull flap and the skull tabs are structured to be attached to the skull with attachment means, thereby reattaching the skull flap to the skull.

2. The strip fastener of claim 1 wherein a sidewall of the strip is adapted to be affixed to the bone edge surface or an edge of the skull.

3. The strip fastener of claim 2 having openings disposed in the sidewall, said openings being selected from the group consisting of holes, slots or slits or a combination of two or more thereof.

4. The strip fastener of claim 1 further comprising floor tabs spaced along the bottom portion of the strip and in between the flap tabs.

* * * * *